United States Patent
Eckhouse et al.

[11] Patent Number: 5,964,749
[45] Date of Patent: *Oct. 12, 1999

[54] METHOD AND APPARATUS FOR SKIN REJUVENATION AND WRINKLE SMOOTHING

[75] Inventors: Shimon Eckhouse; Michael Kreindel, both of Haifa, Israel

[73] Assignee: ESC Medical Systems Ltd., Israel

[*] Notice: This patent issued on a continued prosecution application filed under 37 CFR 1.53(d), and is subject to the twenty year patent term provisions of 35 U.S.C. 154(a)(2).

[21] Appl. No.: 08/529,044

[22] Filed: Sep. 15, 1995

[51] Int. Cl.⁶ .................................................... A61N 5/06
[52] U.S. Cl. ................................................. 606/9; 607/88
[58] Field of Search ..................... 606/2, 3, 8, 9, 606/10; 607/88, 89, 90, 91

[56] References Cited

U.S. PATENT DOCUMENTS

| | | | |
|---|---|---|---|
| 2,699,771 | 1/1955 | Ruttger-Pelli | 607/90 |
| 4,022,534 | 5/1977 | Kishner . | |
| 4,298,005 | 11/1981 | Mutzhas . | |
| 4,608,978 | 9/1986 | Rohr . | |
| 4,686,986 | 8/1987 | Fenyo et al. . | |
| 4,757,431 | 7/1988 | Cross et al. . | |
| 4,784,135 | 11/1988 | Blum et al. . | |
| 4,829,262 | 5/1989 | Furumoto . | |
| 4,930,504 | 6/1990 | Diamantopoulos et al. . | |
| 4,950,880 | 8/1990 | Hayner . | |
| 4,976,709 | 12/1990 | Sand | 606/5 |
| 5,139,494 | 8/1992 | Freiberg | 606/10 |
| 5,161,526 | 11/1992 | Hellwing et al. . | |
| 5,207,671 | 5/1993 | Franken et al. . | |
| 5,217,455 | 6/1993 | Tan . | |
| 5,259,380 | 11/1993 | Mendes et al. . | |
| 5,320,618 | 6/1994 | Gustafsson . | |
| 5,344,418 | 9/1994 | Ghaffari . | |
| 5,344,434 | 9/1994 | Talmore . | |
| 5,591,157 | 1/1997 | Hennings et al. | 606/3 |
| 5,611,795 | 3/1997 | Slatkine et al. | 606/9 |
| 5,660,836 | 8/1997 | Knowlton | 607/96 |

FOREIGN PATENT DOCUMENTS

3906860-A1  3/1989  Germany .

OTHER PUBLICATIONS

Role of Skin Optics in Diagnostic and Therapeutic Uses of Lasers, S. L. Jacques, Springer–Verlag, 1991, pp. 1–21.
Whole–Body Hyperthermia in Cancer Therapy: A Report of A Phase I–II Study, J. van der Zee, et al., Eur. J., Cancer Clinical Oncology, 1983, vol. 19, No. 9, pp. 1189–1200.
Relationship of Response to Transurethral Hyperthermia and Prostate Volume in BPH Patients, Z. Petrovich, F. Ameye, M. Pike, S. Boyd, L. Baert, Urology, 1992, vol. 40, No. 4, pp. 317–321.

(List continued on next page.)

Primary Examiner—Cary O'Connor
Assistant Examiner—Eric F. Winakur
Attorney, Agent, or Firm—Friedman Siegelbaum LLP

[57] ABSTRACT

A method and apparatus for treating skin includes applying pulsed light to the skin to heat and shrinking collagen within the skin, thereby reviving the elasticity of the collagen and of the skin. The epidermis and outer layers of the skin may be protected by cooling with a transparent substance, such as ice or gel, to the skin. The temperature distribution within the skin is controlled by controlling the delay between the time the coolant is applied, and the time the light is applied, by controlling the pulse duration and applying multiple pulses, and by filtering the light and controlling the radiation spectrum, preferably, the spectrum includes light having a wavelength in the range of 600–1200 nm. The pulsed light may be incoherent, such as that produced by a flashlamp, or coherent, such as that produced by a Nd(Yag) laser or a ruby laser, and may be directed to the skin using a flexible or rigid light guide. Also, a method and apparatus for cutaneous resurfacing including directing Er:YAG laser light to the skin. The light may be pulsed, preferably with a delay of about 0.5–10 msec between pulses. In one embodiment the pulses have energy fluences of preferably about 100 J/cm².

18 Claims, 2 Drawing Sheets

OTHER PUBLICATIONS

Nd: YAG Laser–Induced Hyperthermia in A Mouse Tumor Model, S. M. Waldow, P. R. Morrison, L. I. Grossweiner, Lasers in Surgery and Medicine, 1988, vol. 8, No. 5, pp. 510–514.

Light and Electron Microscopic Analysis of Tattoos Treated by O–Switched Ruby Laser, C. Taylor, R. R. Anderson, et al., J. of Investigative Dermatology, 1991, vol. 97, pp. 131–136.

Treatment of Benign Cutaneous Pigmented Lesions with the Candela 510 NM Pulsed Laser, Laser Med. and Surgery Abstracts, R. E. Fitzpatrick, et al., 1992, vol. 4S, p. 73.

Treatment of Pigmented Lesions with the Flashlamp Pumped PLDL ("Brown Spot") Laser, Laser Med. and Surgery Abstracts, G. J. Brauner, M.D., et al., 1992, vol. 4S, p. 73.

Diffusion of Light in Turbid Material, A. Ishimaru, Applied Optics 1989, vol. 28, No. 12, pp. 2210–2215.

METHOD AND APPARATUS FOR SKIN REJUVENATION AND WRINKLE SMOOTHING

FIELD OF THE INVENTION

The present invention relates generally to the art of skin treatment using electromagnetic radiation. More particularly, the invention relates to an efficient method and apparatus for skin rejuvenation by ablation of the outer layer of the skin and wrinkle smoothing (or shrinking) by heating of collagen without damage to the epidermis.

BACKGROUND OF THE INVENTION

There is a strong desire today to obtain and/or maintain a youthful appearance. One manner of doing so is to remove (or reduce) wrinkles. Additionally it is desirable to rejuvenate the skin by removing an outer layer of skin. There are known techniques for removing wrinkles by peeling the skin. Also, there are known methods for rejuvenating the skin. Unfortunately, all known techniques suffer from lack of efficacy and risk to the patient.

One known method of skin rejuvenation includes injection of collagen underneath the skin. This has been performed using a bovine collagen injection. For example, microfine collagen has been injected into periocular lines. Some of the problems with collagen injection include, allergy to collagen and lack of longevity. Also, often there is only partial eradication of the wrinkles.

Peeling most or all of the outer layer of the skin is another known method of rejuvenating the skin. Peeling can be achieved chemically, mechanically or photothermally. Chemical peeling is often carried out using trichloroacetic acid and phenol. An inability to control the depth of the peeling, possible pigmentary change and risk of scarring are among the problems associated with chemical peeling.

The mechanical method is called transcutaneous blepharoplasty and involves shaving off the outer layer of skin. Skin resection during lower lid blepharoplasty frequently results in undesirable side effects, especially ectropion and scleral show. Moreover, transcutaneous blepharoplasty rarely eradicates all of the wrinkle lines.

Pulsed carbon dioxide laser treatment is a known photothermal method of removing of periocular wrinkles. However, laser light is heavily absorbed in water and has a very short range in the epidermis. Thus, a high fluence with short pulse durations will evaporate the outer layer of the skin and peels most or all of the epidermis.

The use of $CO_2$ laser light for skin rejuvenation also has undesirable side effects. For example, $CO_2$ lasers have small spot size (3 mm or less), and thus their use causes valleys and ridges, particularly when resurfacing large areas. Also, it is difficult to control heat diffusion, and thus the resultant necrosis is difficult to predict and control. Additionally, scar tissue absorbs $CO_2$ laser light differently than normal skin and thus may adversely impact such a treatment.

Thus, it is apparent there is a need for a new method and device with which it is possible to produce efficient wrinkle removal and skin rejuvenation. This apparatus would preferably be able to control the treatment parameters according to characteristics of the tissue, and be easily tunable. The new method and device would preferably provide efficient wrinkle smoothing and skin rejuvenation with minimal side effects.

SUMMARY OF THE PRESENT INVENTION

In accordance with one aspect of the invention a method and apparatus for treating skin includes applying pulsed light to the skin to heat and shrinking collagen within the skin, thereby reviving the elasticity of the collagen and of the skin. In one embodiment the method also includes protecting the epidermis and outer layers of the skin by cooling the epidermis and outer layers of the skin. The cooling may be accomplished by applying a cooled transparent substance, such as ice or gel, to the skin.

In one alternative embodiment the skin is cooled by applying the transparent substance to the skin and then cooling it.

In another alternative embodiment the temperature distribution within the skin is controlled by controlling the delay between the time the coolant is applied, and the time the light is applied. A microprocessor may be used for determining the delay time in response to a selected skin temperature profile. Additionally, the temperature distribution may be controlled by controlling the pulse duration and applying multiple pulses. In another embodiment the temperature distribution within the skin is controlled by filtering the light and controlling the radiation spectrum. Preferably, the spectrum includes light having a wavelength in the range of 600–1200 nm.

In another embodiment the pulsed light may be incoherent, such as that produced by a flashlamp, or coherent, such as that produced by an Nd:YAG laser or a ruby laser.

In another embodiment the light is directed to the skin using a flexible or rigid light guide.

In accordance with a second aspect of the invention a method and apparatus for generating a temperature distribution inside a region of skin having a maximum temperature at a selected depth includes cooling the epidermis and outer layers of the skin and applying pulsed light to the skin.

In one embodiment the cooling is accomplished by applying a cooled transparent substance, such as gel or ice, to the skin. Alternatively, the cooling may be accomplished by applying the transparent substance, and then cooling it.

The temperature distribution is further controlled in one embodiment by controlling the delay between the cooling and the light application. In another embodiment the distribution is controlled by controlling the pulse duration and/or applying multiple pulses.

In accordance with a third aspect of the invention a method and apparatus for cutaneous resurfacing includes directing Er:YAG laser light to the skin. The light may be pulsed, preferably with a delay of about 0.5–10 msec between pulses. In one embodiment the pulses have energy fluences of preferably about 100 $J/cm^2$.

In accordance with a fourth aspect of the invention an apparatus for the cutaneous resurfacing of a region of skin, including skin resurfacing or wrinkle smoothing, includes an incoherent light source such as a flashlamp and an Er:YAG laser. The laser can be operated in a multiple pulse mode. A delivery system delivers the incoherent light and laser light to the region to be treated, and the region may be cooled.

Other principal features and advantages of the invention will become apparent to those skilled in the art upon review of the following drawings, the detailed description and the appended claims.

Figure 1:
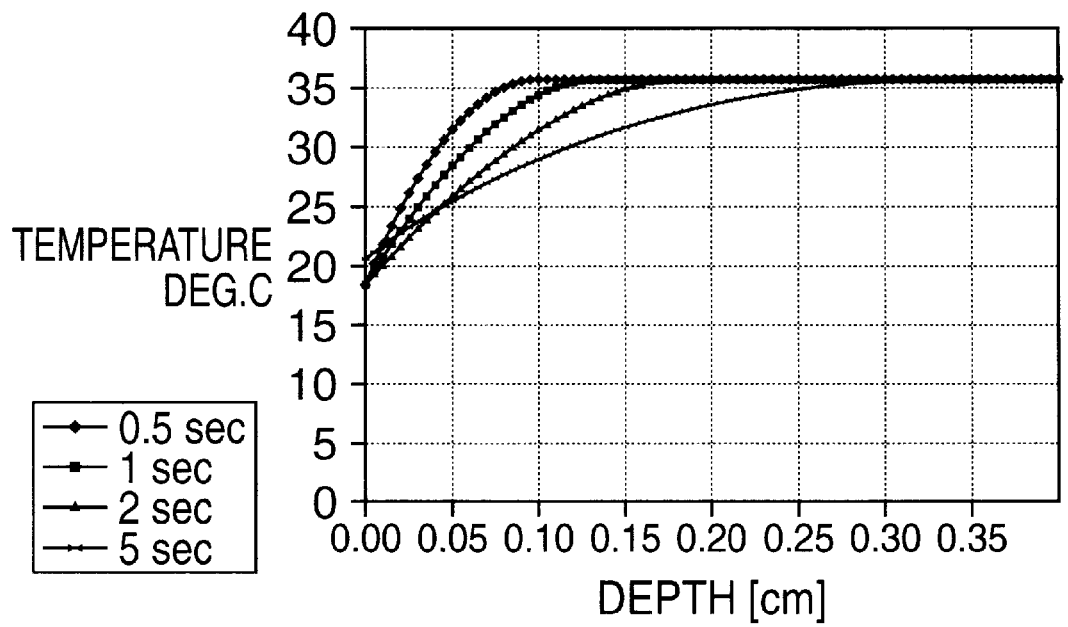
FIG. 1 shows a temperature distribution achieved inside the skin after a cold fluid was applied to the skin, for a plurality of different time delays after the application of the cold gel.

Before explaining at least one embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

The invention relates to a new method and apparatus of removing wrinkle and rejuvenating skin. Generally, in accordance with this invention, wrinkles are smoothed or reduced by collagen molecules shrinking and increasing the elasticity of the skin and collagen, using a short heating impulse (thermal shock). Tissue is heated at a depth of up to a few millimeters by light radiation, while the skin is externally cooled at the surface to avoid overheating the epidermis. The epidermis may be cooled in a variety of ways, including applying a precooled (i.e., a temperature less than the ambient temperature) transparent substance such as ice or cold gel to the skin. The cold substance should cool the skin before and during treatment. The light (electromagnetic radiation) is applied to the skin in pulses shortly after the application of the cooling material. Alternatively, the fluid or gel could be applied to the skin or skin surface, and then cooled (using thermoelectric cooler, e.g.) shortly before the application of the pulsed light to the skin.

The light source will preferably provide a spectrum such that the optical depth of penetration into the tissue is of the order of lam or more. Also, the light source will preferably be able to provide pulses having fluences of the order of 100 J/cm$^2$ and peak power of the order of 1000 W/cm$^2$. A spot size of the order of 10 mm is preferable, to reduce scattering losses.

Laser light sources that should be appropriate include a Nd:YAG laser, a ruby laser, an alexandrite laser, diode lasers and others will be suitable. Incoherent light sources such as a xenon flashlamp should also be appropriate.

A method for cutaneous resurfacing (skin rejuvenation) in accordance with the present invention includes use of an Er:YAG laser light, which has a most efficient wavelength of 2.94 $\mu$m. Because the absorption depth of an Er:YAG laser in skin is very small (less than 20 microns), it may be difficult to ablate to a depth of the order of 100 microns or more (typical of the epidermis) with it. However, a deeper depth of peeling can be achieved by extending the pulse length of the laser. While this is hard to achieve using an Er:YAG laser due to the inherent short level lifetime, by providing a few pulses with a variable delay between the pulses this limitation may be overcome. Evaporated tissue layer thickness may be controlled by the number of pulses and variation of pulse parameters and delay between pulses.

The invention also relates to an apparatus using a flashlamp light source, or any other source with appropriate parameters, for smoothing wrinkles, without damaging the epidermis. Also, an Er:YAG laser is used for efficient skin rejuvenation by removal of the epidermis.

Generally, the device includes a flashlamp that can provide a pulsed light in the range of 600–1200 nm for heating of collagen, a filter system that can cut off the radiation spectrum below approximately 600 nm, a light guide that can provide an appropriate spot size and can provide fluences of the order of 100 J/cm$^2$, and an Er:YAG laser with pulse energy of the order of 1J, which can be operated in multiple pulse mode with delays between pulses of less than 50 msec for skin rejuvenation (by skin ablative peeling).

In one alternative a light source such as a Nd(Yag) laser or ruby laser with appropriate parameters could replace the flashlamp.

This apparatus is very useful for wrinkle removal and skin rejuvenation. A flashlamp light source, particularly when used with external cooling of skin surface, will generate a temperature distribution inside the skin which has a maximum at depth dependent on the light and cooling. Consequently, it is possible to heat collagen molecules without damaging the epidermis. The temperature distribution in the skin is responsive to the delay time between the cooling and application of light, selection of pulse parameters and the radiation spectrum. Accordingly, appropriate control of these parameters allows control of the temperature distribution. An Er:YAG laser operated in multiple pulse mode is very efficient for cutaneous resurfacing procedures and also enables control of depth of evaporation. Thus, the apparatus is safe with little risk of accidental injury to the operator and patient.

As stated above, wrinkles may be smoothed by shrinking collagen molecules using pulsed heating. The present invention method is realized by heating of tissue to depths of up to a few millimeters by light radiation in association with external cooling of skin outer surface to avoid overheating of epidermis. The epidermis may be cooled using many methods. One preferred method is the application of a previously cooled transparent matter like ice or cold gel on the skin which cools the skin before and during treatment. A temperature distribution inside the skin similar to one shown in FIG. 1 is created a short time (of the order of 1 second) after the application of the cooled material.

As may be seen, the distribution is such that the epidermis and the outer layer of the skin are colder than the more deeper part of the skin. However, the applied light heats up the superficial parts of the skin more than the inner parts, because of the attenuation of light energy fluence by depth, and due to higher absorption of light by the epidermis.

Figure 2:
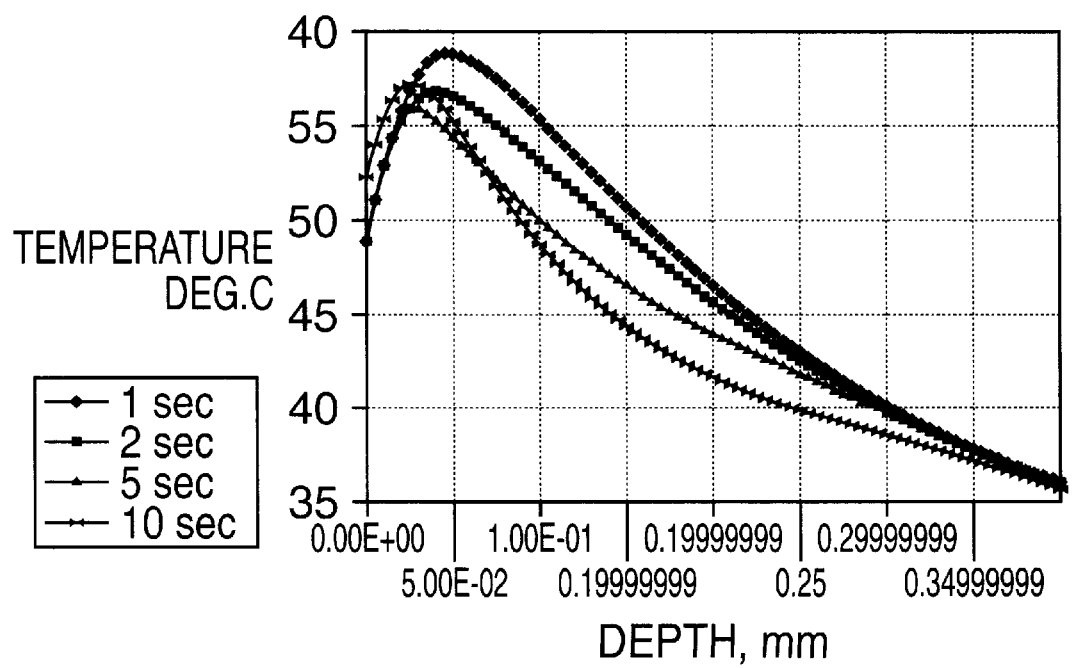
FIG. 2 shows a temperature distribution achieved by precooling the skin and applying the light source.

After heating a temperature distribution such as that shown in FIG. 2 results. As may be seen, the deeper parts of the tissue are heated up to a temperature sufficient to cause collagen shrinking, but without damaging the outer parts of the skin (epidermis).

The temperature distribution generated prior to the application of light (FIG. 1) is a function of the initial temperature of the cooling material and the delay time between the application of the cooling material and the application of light. By varying this time the depth of penetration of the "cool front" can be varied. When collagen that is deeper needs to be treated without influencing the superficial skin, a longer delay time between the application of the coolant and the light can be used. When the superficial collagen needs to be treated, a shorter delay time can be used.

In a typical treatment the doctor applies the cold gel to the skin before treatment and then applies the light source. In accordance with one embodiment of the invention, the treatment device indicates to the doctor when the light source needs to be applied after application of the cooling material, to achieve a desired temperature distribution. A microprocessor that controls the light generating device may also generate a timing signal for the doctor to accomplish this aspect of the invention.

The applicants have determined that a light source having the following parameters is suitable for implementing the invention.

Light radiation should penetrate into a tissue at a millimeter depth. Examples of light sources which meet the parameter include flashlamp, diode laser, Nd:YAG laser and ruby laser.

Optical power should be on the order of 100–1000 W/cm$^2$.

Fluence should be on the order of 30–150 J/cm$^2$.

Spot size should be on the order of a few millimeters to some centimeters, preferably variable over a range.

Figure 3:
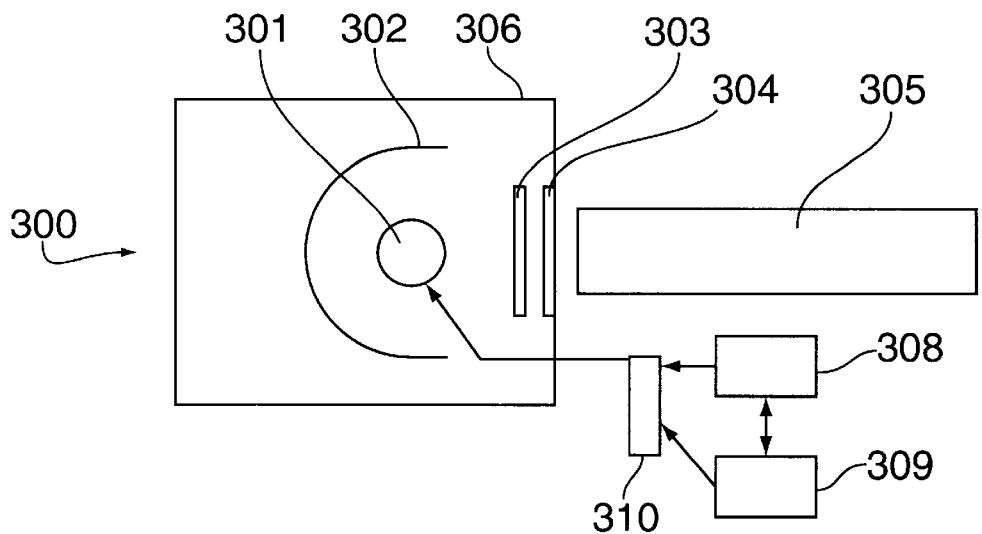
FIG. 3 is a schematic illustration of the flashlamp light source according to one preferred embodiment of the present invention.
Figure 4:
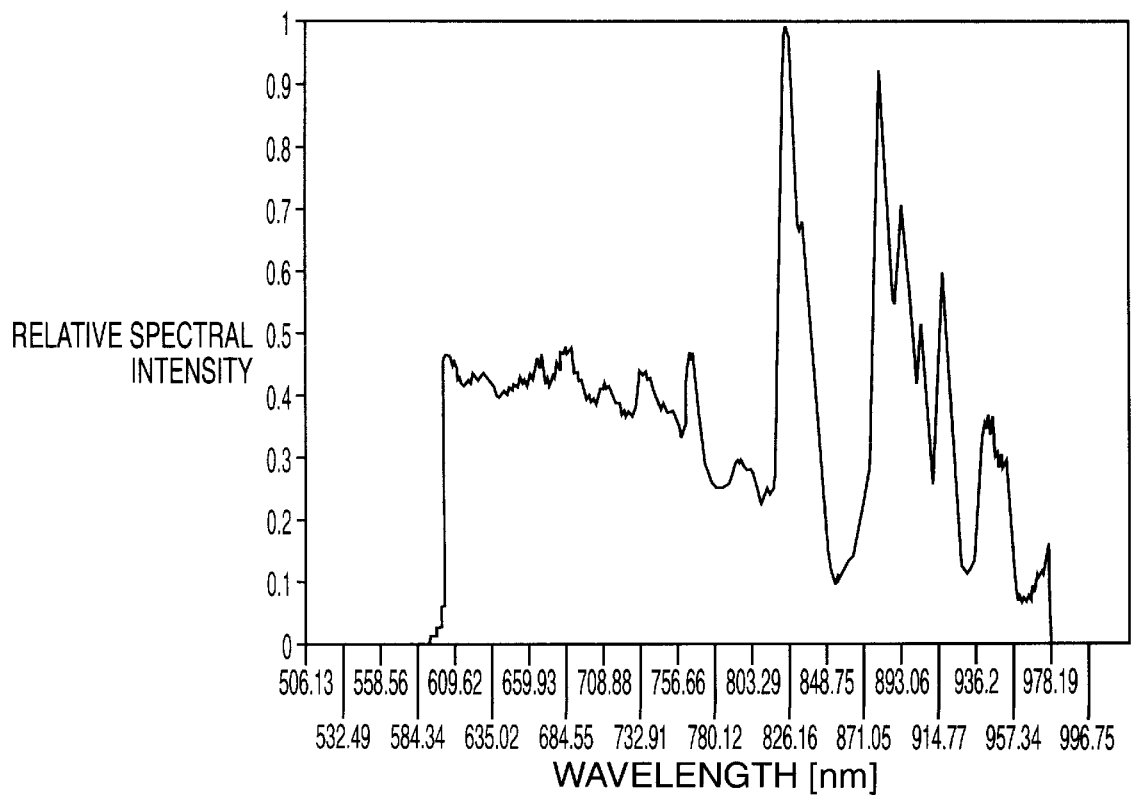
FIG. 4 shows a normalized output filtered radiation spectrum of a flashlamp light source.

A detailed description of one preferred embodiment will be described with reference to FIG. 3. As shown in FIG. 3, a treatment device 300 includes a flashlamp 301 which can be operated in pulse mode, a reflector 302 which forms a light beam and conducts it to a light guide 305 through a filter system 303 and 304. Reflector 302 is located in a treatment head (or housing) 306.

Filter system 303 and 304 may include one or more filters which cut off the radiation spectrum at approximately 550(or 600)–800 nm. Filter 303 provides reflection of the part of unused incident radiation and avoids overheating of absorbing filter 304. Absorbing filter cuts off radiation at approximately 550–800 nm. Flexible light guide 305 can be interchanged with a rigid light guide made out of quartz or other types of high optical quality glass. Treatment head 305 is useful for treating large areas.

According to one embodiment, the light energy is applied to the skin using a train of pulses. One advantage of applying a train of pulses is that the epidermis cools relative to the layer of collagen that is heated in the treatment. Preferably, the apparatus produces a train of pulses with variable delays between pulses in the range of 10's to 100's of milliseconds.

The total number of pulses per pulse train can also be varied. More specifically, for a patient with higher skin absorption due to heavier skin pigmentation a larger number of pulses per train is preferably used.

Similarly, the pulse duration of each pulse in the train can also be varied in order to enable cooling of the epidermis without cooling the collagen. In any event, the total dose to the treated area is the product of the number of pulses and the fluence per pulse. The pulse duration, and train length are controlled in one embodiment by a microprocessor 309. As shown on FIG. 3, microprocessor 309 provides control signals to pulse forming network 310. Pulse forming network 310 (generally of the type described in commonly owned U.S. Pat. No. 5,405,368, which is incorporated herein by reference) provides pulse to flashlamp 301.

The radiation spectrum can be controlled by filter system 303 and 304. Additionally (or alternatively), the spectrum of radiation can be controlled by varying the current density through the flashlamp. If deeper heating is required a longer wavelength radiation is used. Pulse duration may be varied in the range of a few milliseconds to a few ten's of milliseconds.

Other embodiments of the present invention include the use of lasers (those having proper penetration), which can also be very effective to smooth wrinkles. For example, a flashlamp pumped Nd:YAG laser operating at 1.06 $\mu$m can provide deep penetration and thus be effective. The laser may be operated in the pulsed train mode, preferably by pulsing the flashlamps that are used to pump the laser. Similarly, a ruby laser may be used. However, the pulse duration cannot be made too long due to the limited value of the lifetime of the lasing level of these lasers. In the laser embodiment, there is no need for filters since the light is monochromatic. Also this embodiment does not require the use of a rigid light guide since flexible light guides are readily available for laser applications and a low divergence laser beam can be easily focused into a small diameter optical fiber. The use of multiple pulses may be particularly useful to overcome the limited lasing level in the laser embodiment of the invention.

The cutaneous resurfacing method in accordance with the present invention includes an Er:YAG laser light, whose radiation has an absorption depth of much less than that of $CO_2$ laser radiation, of the order of 50 micron is used. Despite the relatively low absorption depth, an appropriate peeling depth is reached by providing multiple pulses. The thickness of the layer of evaporated tissue may be controlled by the number of pulses, the delay between pulses and varying pulse parameters.

Er:YAG lasers produce radiation of 2.94 $\mu$m, with an energy per pulse of up to 1J. Absorption depth of the radiation is typically about 10 $\mu$m. Thus, to evaporate an epidermis, a train of pulses should be used. Typical delay between the laser pulses should be in the range of 0.5–10 msec. The time should preferably be shorter than, or on the order of, the epidermis thermal relaxation time.

Thus, it should be apparent that there has been provided in accordance with the present invention a treatment device that includes a flashlamp or a near infrared pulsed laser in another embodiment, an Er:YAG laser and a coupler that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The embodiments of the invention in which an exclusive property or privilege is claimed are defined as follows:

1. An apparatus for treating a region of skin comprising;
    a pulsed light source for heating and shrinking the collagen in the region of skin to a degree sufficient to reduce wrinkles in the region of skin;
    a housing in which the pulsed light source is disposed, wherein the housing includes an aperture disposed with respect to the pulsed light source to direct light emitted from the light source to the region of skin; and
    a timer, connected to the pulsed light source, for indicating when a delay time has passed after an application of a cooling substance to the skin region.

2. The apparatus of claim 1 wherein the pulsed light source includes a microprocessor for determining the delay time in response to a selected skin temperature profile.

3. The apparatus of claim 1 wherein the pulsed light source includes a microprocessor for determining the delay time in response to a selected collagen heating depth.

4. The apparatus of claim 1, including means for reducing the temperature of the cooling substance, wherein the means for reducing is disposed to provide a signal indicative of cooling to the timer.

5. The apparatus of claim 1 wherein the pulsed light source includes a noncoherent light source.

6. The apparatus of claim 1 further including a filter disposed adjacent to the aperture, wherein a temperature distribution within the skin is controlled in response to a radiation spectrum produced by filtering the light.

7. The apparatus of claim 1 wherein the filter is of the type that does not eliminate light having a wavelength in the range of 600–1200 nm.

8. A method of cutaneous resurfacing of a region of skin by removing at least an outer layer of skin in the region comprising the steps of:

produce Er:YAG laser light; and directing the light to the region of skin for a duration and with an intensity sufficient to remove an outer layer of skin;

waiting for a period of time not less than the thermal relaxation time of the skin; and repeating the step of directing the light.

9. The method of claim 8, wherein the step of producing includes the step of pulsing the laser light.

10. The method of claim 9, wherein the step of pulsing includes the step of delaying in the range of 0.5–10 msec between pulses.

11. The method of claim 9, wherein the step of pulsing includes the step of providing pulses having energy fluences on the order of 100 J/cm$^2$.

12. An apparatus for skin rejuvenation by removing at least an outer layer of skin in a region of skin comprising:

an Er:YAG laser light source disposed in a housing capable of directing light to the region of skin for a duration and with an intensity sufficient to remove the outer layer;

a pulse forming circuit coupled to the Er:YAG laser light source including a pulse delay circuit for providing a delay between sequential pulses of Er:YAG light for a period of time not less than the thermal relaxation time of the skin.

13. The apparatus of claim 12, wherein the pulse delay circuit produces a delay in the range of 0.5–10 msec between pulses.

14. The apparatus of claim 12, wherein the light source is capable of providing pulses having energy fluences on the order of 100 J/cm$^2$.

15. An apparatus for the cutaneous resurfacing of a region of skin, including skin resurfacing and wrinkle smoothing, which comprises:

an incoherent light source such as a flashlamp for generating incoherent light for heating collagen to a temperature sufficient to reduce wrinkling;

an Er:YAG laser which can be operated in multiple pulse mode for generating laser light; and a delivery system disposed to deliver the incoherent light and laser light to the region.

16. A method of smoothing wrinkles in a region of wrinkled skin comprising the steps of:

applying a pulsed light to a surface of the region of wrinkled skin, said step of applying pulsed light including the step of pulsing a non-coherent light source; and heating collagen in the region of the wrinkled skin to a temperature that will shrink the collagen sufficiently to reduce the wrinkles.

17. The method of claim 16, further including the step of controlling the radiation spectrum by filtering the light to control a temperature distribution within the skin.

18. The method of claim 17 further including the steps of controlling a pulse duration and applying multiple pulses to control a temperature distribution within the skin.

* * * * *

(12) EX PARTE REEXAMINATION CERTIFICATE (6732nd)
United States Patent
Eckhouse et al.

(10) Number: US 5,964,749 C1
(45) Certificate Issued: Mar. 31, 2009

(54) METHOD AND APPARATUS FOR SKIN REJUVENATION AND WRINKLE SMOOTHING

(75) Inventors: Shimon Eckhouse, Haifa (IL); Michael Kreindel, Haifa (IL)

(73) Assignee: Lumenis Ltd., Yokneam (IL)

Reexamination Request:
No. 90/010,070, Dec. 5, 2007
No. 90/010,154, Apr. 29, 2008

Reexamination Certificate for:
Patent No.: 5,964,749
Issued: Oct. 12, 1999
Appl. No.: 08/529,044
Filed: Sep. 15, 1995

(51) Int. Cl.
*A61N 5/06* (2006.01)

(52) U.S. Cl. .............................. 606/9; 607/88
(58) Field of Classification Search .................. None
See application file for complete search history.

(56) References Cited

U.S. PATENT DOCUMENTS

| | | | |
|---|---|---|---|
| 2,716,698 A | 8/1955 | Brukner | 240/1 |
| 2,954,771 A | 10/1960 | Boyan | 128/396 |
| 3,327,712 A | 6/1967 | Kaufman et al. | 128/398 |
| 3,693,623 A | 9/1972 | Harte et al. | 128/303.1 |
| 3,834,391 A | 9/1974 | Block | 128/303.1 |
| 3,930,504 A | 1/1976 | de Laforcade | 128/303.1 |
| 4,229,658 A | 10/1980 | Gonser | 250/504 H |
| 4,233,493 A | 11/1980 | Nath | 219/354 |
| 4,283,661 A | 8/1981 | Doty | 315/360 |
| 4,298,005 A | 11/1981 | Mutzhas | 128/396 |

(Continued)

FOREIGN PATENT DOCUMENTS

| | | |
|---|---|---|
| DE | 27 17 421 A1 | 11/1978 |
| JP | 4-90360 | 8/1992 |
| SE | 465 953 B | 11/1991 |
| WO | WO 89/00871 | 2/1989 |
| WO | WO 90/14836 | 12/1990 |
| WO | WO-91/15264 | 10/1991 |
| WO | WO 91/15264 | 10/1991 |
| WO | WO 98/52645 | 11/1998 |

OTHER PUBLICATIONS

Gros, et al, Diaphanologie Mammaire, Memoires Originaux, *J. Radiol. Electrol.*, 53(4):297–306 (1972), in French, with English translation.
Brochure for an Infrared Coagulator by Redfield Corporation (1968).
Achauer et al., "Argon Laser Treatment of Telangiectasia of the Face and Neck: 5 Years' Experience", *Lasers Surg. Med.*, 7:495–498 (1987).
Alora et al., "Recent Developments in Cutaneous Lasers", *Lasers Surg. Med.*, 26:108–118 (2000).

(Continued)

*Primary Examiner*—Beverly M. Flanagan

(57) ABSTRACT

A method and apparatus for treating skin includes applying pulsed light to the skin to heat and shrinking collagen within the skin, thereby reviving the elasticity of the collagen and of the skin. The epidermis and outer layers of the skin may be protected by cooling with a transparent substance, such as ice or gel, to the skin. The temperature distribution within the skin is controlled by controlling the delay between the time the coolant is applied, and the time the light is applied, by controlling the pulse duration and applying multiple pulses, and by filtering the light and controlling the radiation spectrum, preferably, the spectrum includes light having a wavelength in the range of 600-1200 nm. The pulsed light may be incoherent, such as that produced by a flashlamp, or coherent, such as that produced by a Nd(Yag) laser or a ruby laser, and may be directed to the skin using a flexible or rigid light guide. Also, a method and apparatus for cutaneous resurfacing including directing Er:YAG laser light to the skin. The light may be pulsed, preferably with a delay of about 0.5-10 msec between pulses. In one embodiment the pulses have energy fluences of preferably about 100 J/cm$_2$.

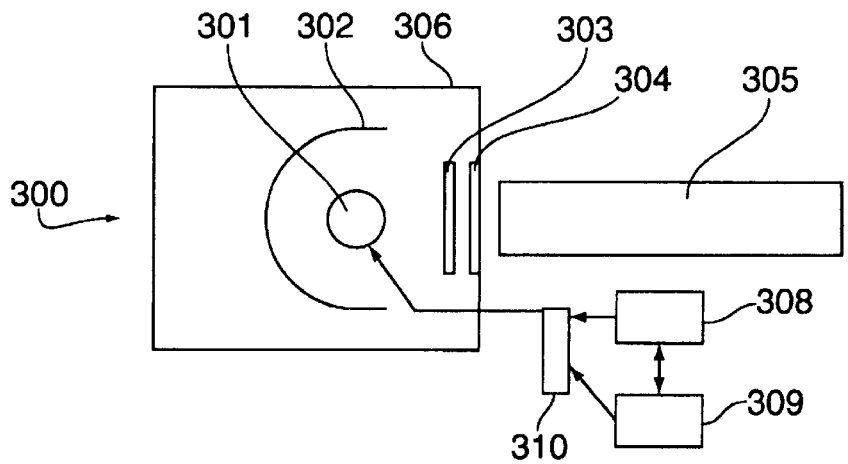

U.S. PATENT DOCUMENTS

| | | | |
|---|---|---|---|
| 4,321,930 A | 3/1982 | Jobsis et al. | 128/633 |
| 4,366,883 A | 12/1982 | Bees | 372/70 |
| 4,380,240 A | 4/1983 | Jobsis et al. | 128/633 |
| 4,388,924 A | 6/1983 | Weissman et al. | 128/303.1 |
| 4,444,190 A | 4/1984 | Mutzhas | 128/396 |
| 4,497,018 A | 1/1985 | Rice | 363/96 |
| 4,506,196 A | 3/1985 | Bees | 315/241 R |
| 4,539,987 A | 9/1985 | Nath et al. | 128/303.1 |
| 4,560,883 A | 12/1985 | Kerschgens | 250/504 |
| 4,564,011 A | 1/1986 | Goldman | 128/303.1 |
| 4,645,980 A | 2/1987 | Yang | 315/159 |
| 4,647,830 A | 3/1987 | Bees | 320/1 |
| 4,653,495 A | 3/1987 | Nanaumi | 128/303.1 |
| 4,672,969 A | 6/1987 | Dew | 128/397 |
| 4,726,377 A | 2/1988 | Jegers et al. | 128/376 |
| 4,729,375 A | 3/1988 | Jegers et al. | 128/376 |
| 4,733,660 A | 3/1988 | Itzkan | 128/303.1 |
| 4,775,361 A | 10/1988 | Jacques et al. | 604/20 |
| 4,810,658 A | 3/1989 | Shanks et al. | 436/172 |
| 4,829,262 A | 5/1989 | Forumoto | 330/4.3 |
| 4,835,749 A | 5/1989 | Welton | 368/10 |
| 4,839,562 A | 6/1989 | Francis et al. | 315/149 |
| 4,851,738 A | 7/1989 | Yang | 315/159 |
| 4,871,559 A | 10/1989 | Dunn et al. | 426/248 |
| 4,884,568 A | 12/1989 | Hahn | 128/303.1 |
| 4,930,504 A | 6/1990 | Diamantopoulos et al. | 128/395 |
| 4,938,221 A | 7/1990 | Tuffel | 128/401 |
| 4,947,859 A | 8/1990 | Brewer et al. | 128/715 |
| 5,008,579 A | 4/1991 | Conley et al. | 310/303 |
| 5,020,995 A | 6/1991 | Levy | 433/215 |
| 5,034,235 A | 7/1991 | Dunn et al. | 426/238 |
| 5,039,867 A | 8/1991 | Nishihara et al. | 250/492.3 |
| 5,054,488 A | 10/1991 | Muz | 128/633 |
| 5,059,192 A | 10/1991 | Zaias | 606/9 |
| 5,066,293 A | 11/1991 | Furumoto | 606/9 |
| 5,071,422 A | 12/1991 | Watson et al. | 606/128 |
| 5,083,093 A | 1/1992 | Adler et al. | 328/65 |
| 5,113,462 A | 5/1992 | Clancy et al. | 385/53 |
| 5,125,922 A | 6/1992 | Dwyer et al. | 606/3 |
| 5,126,621 A | 6/1992 | Morton et al. | 313/237 |
| 5,194,723 A | 3/1993 | Cates et al. | 250/205 |
| 5,204,517 A | 4/1993 | Cates et al. | 250/205 |
| 5,226,107 A | 7/1993 | Stern et al. | 392/416 |
| 5,269,778 A | 12/1993 | Rink et al. | 606/12 |
| 5,281,798 A | 1/1994 | Hamm et al. | 250/205 |
| 5,282,797 A | 2/1994 | Chess | 606/9 |
| 5,290,273 A | 3/1994 | Tan | 606/9 |
| 5,290,274 A | 3/1994 | Levy et al. | 606/13 |
| 5,312,395 A | 5/1994 | Tan et al. | 606/9 |
| 5,320,618 A | 6/1994 | Gustafsson | 606/9 |
| 5,328,488 A | 7/1994 | Daikuzono | 606/16 |
| 5,328,517 A | 7/1994 | Cates et al. | 134/7 |
| 5,334,190 A | 8/1994 | Seiler | 606/5 |
| 5,337,741 A | 8/1994 | Diamond | 600/8 |
| 5,344,418 A | 9/1994 | Ghaffari | 606/9 |
| 5,344,433 A | 9/1994 | Talmore | 607/88 |
| 5,374,265 A | 12/1994 | Sand | 606/9 |
| 5,400,791 A | 3/1995 | Schlier et al. | 128/664 |
| 5,423,803 A | 6/1995 | Tankovich et al. | 606/9 |
| 5,445,146 A | 8/1995 | Bellinger | 607/89 |
| D363,349 S | 10/1995 | Dittert | D24/158 |
| 5,474,528 A | 12/1995 | Meserol | 604/20 |
| 5,489,279 A | 2/1996 | Meserol | 604/290 |
| 5,522,814 A | 6/1996 | Bernaz | 606/36 |
| 5,546,214 A | 8/1996 | Black et al. | 359/203 |
| 5,558,666 A | 9/1996 | Dewey et al. | 606/9 |
| 5,595,568 A | 1/1997 | Anderson et al. | 606/9 |
| 5,618,284 A | 4/1997 | Sand | 606/5 |
| 5,725,565 A | 3/1998 | Smith | 607/88 |
| 5,755,753 A | 5/1998 | Knowlton | 607/98 |
| 5,814,040 A | 9/1998 | Nelson et al. | 606/9 |
| 5,817,089 A | 10/1998 | Tankovich et al. | 606/9 |
| 5,817,090 A | 10/1998 | Abergel et al. | 606/9 |
| 5,843,143 A | 12/1998 | Whitehurst | 607/88 |
| RE36,634 E | 3/2000 | Ghaffari | 606/9 |
| 6,171,332 B1 | 1/2001 | Whitehurst | 607/89 |

OTHER PUBLICATIONS

Alster et al., "Treatment of Port–Wine Stains with the Flashlamp–pumped Pulsed Dye Laser: Extended Clinical Experience in Children and Adults", *Ann. Plast. Surg.*, 32(5):478–484 (1994).

Altshuler et al., "Extended Theory of Selective Photothermolysis", *Lasers Surg. Med.*, 29:416–432 (2001).

Ambrose et al., "Prospective randomized comparison of photocoagulation and rubber band ligation in treatment of haemorrhoids", *Br. Med. J.*, 286:1389–1391 (1983).

Anderson et al., "Mechanisms of Selective Vascular Changes Caused by Dye Lasers", *Lasers Surg. Med.*, 3:211–215 (1983).

Anderson et al., "Microvasculature Can Be Sensitively Damaged Using Dye Lasers: A Basic Theory and Experimental Evidence in Human Skin", *Lasers Surg. Med.*, 1:263–276 (1981).

Anderson et al., "Selective Photothermolysis: Precise Microsurgery by Selective Absorption of Pulsed Radiation", *Science*, 220:524–527 (1983).

Anderson, T.F., "Light Sources in Photomedicine", in *Clinical Photomedicine*, Chapter 3, pp. 37–58, Marcel Dekker, Inc., New York (1993).

Angermeier, M.C., "Treatment of facial vascular lesions with intense pulsed light", *J. Cutan. Laser Ther.*, 1:95–100 (1999).

Anvari et al., "Selective cooling of biological tissues: application for thermally mediated therapeutic procedures", *Phys. Med. Biol.*, 40:241–252 (1995).

Apfelberg et al., "Comparison of Argon and Carbon Dioxide Laser for Treatment of Decorative Tattoos Clinical and Pathological Observations", *Lasers Surg. Med.*, 3:183 (Abstract No. 294) (1983).

Apfelberg et al., Dot or Pointillistic Method for Improvement in Results of Hypertrophic Scarring in the Argon Laser Treatment of Portwine Hemangiomas, *Lasers Surg. Med.*, 6:552–558 (1987).

Apfelberg et al., "Investigation of YAG Laser Uses in Plastic Surgery", *Lasers Surg.*, 6:246 (Abstract No. 77) (1986).

Apfelberg et al., "Preliminary Investigation of KTP/532 Laser Light in the Treatment of Hemangiomas and Tattoos", *Lasers Surg. Med.*, 6:38–42 (1986).

Apfelberg et al., "Progress Report on Extended Clinical Use of the Argon Laser for Cutaneous Lesions", *Lasers Surg. Med.*, 1:71–83 (1980).

Apfelberg et al., "Progress Report on Multicenter Study of Laser–Assisted Liposuction", *Aesth. Plast. Surg.*, 18:259–264 (1994).

Apfelberg et al., "Results of Argon and CO2 Laser Exposure of Telangiectasia of the Lower Extremity: A Preliminary Report", *Lasers Surg. Med.*, 3:149 (Abstract No. 165) (1983).

Apfelberg et al., "Study of Three Laser Systems for Treatment of Superficial Varicosities of the Lower Extremity", *Lasers Surg. Med.*, 7:219–223 (1987).

Apfelberg et al., "Superpulse $CO_2$ Laser Treatment of Facial Syringomata", *Lasers Surg. Med.*, 7:533–537 (1987).

Apfelberg et al., "Update on Laser Usage in Treatment of Decorative Tattoos", *Lasers Surg. Med.*, 2:169–177 (1982).

Apfelberg, D.B., "Intralesional Laser Photocoagulation—Steroids as an Adjunct to Surgery for Massive Hemangiomas and Vascular Malformations", *Ann. Plast. Surg.*, 35:144–148 (1995).

Ara et al., "Irradiation of Pigmented Melanoma Cells with High Intensity Pulsed Radiation Generates Acoustic Waves and Kills Cells", *Lasers Surg. Med.*, 10:52–59 (1990).

Ashinoff et al., "Cappillary Hemangiomas and Treatment with the FlashLamp–Pumped Pulsed Dye Laser", *Arch. Dermatol.*, 127:202–205 (1991).

Ashinoff et al., "Flashlamp–pumped pulsed dye laser for port–wine stains in infancy: Earlier versus later treatment", *J. Am. Acad. Dermatol.*, 24:467–472 (1991).

Bell et al., "100 µsec pulsed $CO_2$ laser resurfacing of lower eyelids: Erythema and rhytides reduction", *SPIE*, 2970:360–366 (1997).

Broska et al., "Comparison of the Argon Tunable Dye Laser with the Flashlamp Pulsed Dye Laser in Treatment of Facial Telangiectasia", *J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–594 (1991).

Burson et al., "Gel de Transmision de Ultrasonidos: Estudio Comparitivo de Distintas Formulaciones", *Farm Hosp.*, pp. 394–399 (1991) (in Spanish, with English Abstract Only).

Cates, M.C., "A long pulse (5 µs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremities", *J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL", *J. Cutan. Laser Ther.*, 1:101–104 (1999).

Cole–Beuglet et al., "Ultrasound mammography for the Augmented Breast", *Radiology*, 146:737–742 (1983).

Colver et al., "Port Wine Stains", *J. Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "A History of Photodynamic Therapy", *Aust. N. Z. J. Surg.*, 61:340–348 (1991).

Denham et al., "Light Distribution in Laser Irradiated Tissue", *Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulos et al., "High–energy Short–pulse Flashlamps: Operating Characteristics", *Applied Optics*, 16:70–75 (1977).

Ell et al., "Laser Lithotripsy of Gallstone by Means of a Pulsed Neodymium YAG Laser—In Vitro and Animal Experments", *Endoscopy*, 18:92–94 (1986).

Englehardt et al., "Spectroscopy During Laser Induced Shock Wave Lithotripsy", *SPIE*, 906:200–204 (1988).

Fitzpatrick et al., "Flashlamp–pumped Pulsed Dye Laser Treatment of Port–Wine Stains", *J. Dermatol. Surg. Oncol.*, 20:743–748 (1994).

Fitzpatrick et al., "Treatment of Leg Veins: A Comparison of Laser Therapy with a Noncoherent, Multiwave Light Source", *Proc. Ann. Meeting IEEE Lasers & Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study", *Lasers Med. Sci.*, 8:185–196 (1993).

Foster et al., "The Successful Use of the PhotoDerm VL in the Treatment of a Cavernous Hemangioma in a Dark–Skinned Infant", *Minimally Invasive Surgical Nursing*, 10:102–104 (1996).

Garden et al., "Effect of Dye Laser Pulse Duration on Selective Cutaneous Vascular Injury", *J. Invest. Dermatol.*, 87(5):653–657 (1986).

Garden et al., "The Treatment of Port–wine Stains by the Pulsed Dye Laser: Analysis of Pulse Duration and Long–term Therapy", *Arch. Dermatol.*, 124:889–896 (1988).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Lasers Surg. Med.*, 11:287–296 (1991).

Gijsbers et al., "Effect of Force on Ablation Depth for a XeCI Excimer Laser Beam Delivered by an Optical Fiber in Contact with Arterial Tissue Under Saline", *Lasers Surg. Med.*, 12:576–584 (1992).

Gilbert, D.J., "Incorporating Photodynamic Therapy Into a Medical and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long–Term Hair Removal", *J. Cutan. Laser. Ther.*, 1:167–171 (1999).

Gold et al., "Treatment of Wrinkles and Skin Tightening Using Aluma™ Skin Renewal System with FACES™ (Functional Aspiration Controlled Electrothermal Stimulation) Technology", *Aesthetic Buyers Guide*, pp. 1–6 (2005).

Gold, M.H., "Aminolevulinic Acid Photodynamic Therapy: Medical Evidence for Its Expanded Use", *Expert Rev. Med. Devices*, 3:357–371 (2006).

Gold, M.H., "Introduction to Photodynamic Therapy: Early Experience", *Dermatol. Clin.*, 25:1–4 (2007).

Goldberg et al., "Nonablative Treatment of Rhytids With Intense Pulsed Light", *Lasers Surg. Med.*, 26:196–200 (2000).

Goldberg et al., "Q–switched Nd:YAG Laser: Rhytid Improvement by Non–Ablative Dermal Remodeling", *J. Cutan. Laser Ther.*, 2:157–160 (2000).

Goldberg, D.J., "Effect of Temperature–Controlled Cooling on Light–Based Skin Treatments", *J. Cos. Laser Ther.*, 8:155–156 (2006).

Goldberg, D.J., "Erbium: YAG Laser Resurfacing: What Is Its Role?", *Aesth. Surg. J.*, 18(4):255–260 (1998).

Goldberg, D.J., "New Collagen Formation After Dermal Remodeling with an Intense Pulsed Light Source", *J. Cutan. Laser Ther.*, 2:59–61 (2000).

Goldman et al., "600 nm Flash Pumped Dye Laser for Fragile Telangiectasia of the Elderly", *Lasers Surg. Med.*, 13:227–233 (1993).

Goldman et al., "Photothermal Sclerosis of Leg Veins", *Dermatol. Surg.*, 22:323–330 (1996).

Goldman et al., "Pulsed dye laser treatment of telangiectases with and without subtherapeutic sclerotherapy", *J. Am. Acad. Dermatol.*, 23(1):23–30 (1990).

Goldman et al., "Treatment of Cutaneous Vascular Lesions", in *Cutaneous Laser Surgery*, Chapter 2, pp. 19–105 (1994).

Goldman et al., "Treatment of port–wine stains (capillary malformation) with the flashlamp–pumped pulsed dye laser", *J. Pediatrics*, 122(1):71–77 (1993).

Goldman, M.P., "Laser and Noncoherent Pulsed Light Treatment of Leg Telangiectasia and Venules", *Cos. Dermatol.*, 8(10):43–44 (1995).

Goldman, M.P., "Sclerotherapy Treatment for Varicose and Telangiectatic Leg Veins", in *Vascular and Pigmented Abnormalities*, Chapter 17, pp. 256–271 (1997).

Gomer, H., "Military laser burns away skin flaws", *The Lond Sunday Times*, No. 8929 (Oct. 15, 1995).

Gonzalez et al., "Treatment of telangiectases and other benign vascular lesions with the 577 nm pulsed dye laser", *J. Am. Acad. Dermatol.*, 27(2):220–226 (1992).

Gregory et al., "Effect of Blood Upon the Selective Ablation of Atherosclerotic Plaque with a Pulsed Dye Laser", *Lasers Surg. Med.*, 10:533–543 (1990).

Grevelink et al., "Update on the Treatment of Benign Pigmented Lesions with the Q–Switched Ruby Lasers", *Laser Surg. Med.*, 4:73–74 (Abstract No. 326) (1992).

Groot et al., "Comparison of the infrared coagulator and the carbon dioxide laser in the removal of decorative tattoos", *J. Am. Acad. Dermatol.*, 15:518–522 (1986).

Gustafsson et al., "A Variable Pulsewidth Vascular System for Dermatology", *SPIE*, 2128:188–196 (1994).

Guttman, C., "Novel radiofrequency–based treatment achieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE*, 2671:211–218 (1996).

Henderson, B.W., "Photodynamic therapy—coming of age", *Photodermatology*, 6:200–211 (1989).

Henning et al., "Clinical and Histological Evaluation of Portwine Stain Treatment with a Microsecond pulsed Dye–laser at 577 NM", *Lasers Surg. Med.*, 4:375–380 (1984).

Henning et al., "Port Wine Stain Coagulation Experiments with a 540–nm Continuous Wave Dye–laser", *Lasers Surg. Med.*, 2:205–210 (1983).

Henning et al., "Rhinophyma Treated by Argon Laser", *Lasers Surg. Med.*, 2:211–215 (1983).

Henning et al., "Treatment of Keloids and Hypertrofic Scars with an Argon Laser", *Lasers Surg. Med.*, 6:72–75 (1986).

Hilsenrath, J.E., "Investing it; Unsightly Veins? Zap. Wall St. Woes? Zap.", *New York Times*, http://www.nytimes.com, pp. 1–3 (Jun. 23, 1996).

Hruza et al., "Laser Skin Resurfacing", *Arch. Dermatol.*, 132:451–455 (1996).

Hughes, P.S.H., "Multiple Miliary Osteomas of the Face Ablated With the Erbium: YAG Laser", *Arch. Dermatol.*, 135:378–380 (1999).

"Infrared–Coagulator", Lumatec product leaflet, pp. 1–4.

Ishimaru, A., "Diffusion of light in turbid material", *Applied Optics*, 28(12):2210–2215 (1989).

Jacques, S.L., "The Role of Skin Optics in Diagnostic and Therapeutic Uses of Lasers", *Lasers Dermatol.*, pp. 1–21 (1992).

Jaitly et al., "1 MV Long Pulse Generator with Low Ripple and Low Droop", *8th IEEE Int'l Pulsed Power Conf.*, pp. 161–165 (1991).

Jaitly et al., "Design and Testing of Multi–output 300 kV Prototype Induction Cell Pulsed Power Supply for Darht", *10th IEEE Int'l Pulsed Power Conf.*, pp. 1412–1421 (1995).

Jay, H.H., "Victory Over Veins", http://www.nytimes.com, pp. 1–2 (Jul. 21, 1996).

Johannigmann et al., "Ein Neues Ultraschall–Kontaktgel", *Geburtsh. U. Frauenheilk*, p. 34 (1974) (in German, with English Abstract Only).

Kalka et al., "Photodynamic Therapy in Dermatology", *J. Am. Acad. Dermatol.*, 42:389–413 (2000).

Kaminester, L.H., "Suntanning Centers", *JAMA*, 244(11):1258–1259 (1980).

Kaufmann et al., "Pulsed 2·94–μm erbium–YAG laser skin ablation–experimental results and first clinical application", *Clin. Exp. Dermatol.*, 15:389–393 (1990).

Keijzer et al., "Laser Beam Diameter for Port Wine Stain Treatment", *Lasers Surg. Med.*, 11:601–605 (1991).

Kennedy et al., "Photodynamic Therapy with Endogenous Protoporphyrin, IX: Basic Principles and Present Clinical Experience", *J. of Photochem. Photobio.*, 6:143–148 (1990).

Kilmer et al., "Pulse Dye Laser Treatment of Rhytids", *Lasers Surg. Med.*, p. 44 (Abstract No. 194) (1997).

Koechner, W., in *Solid State Laser Engineering*, Springer Series in Optical Sciences—vol. 1, Chapters 1–2, pp. 1–620, Springer–Verlag, New York (1976).

Lakmaker et al., "Modeling the Color Perception of Port Wine Stains and its Relation to the Depth of Laser Coagulated Blood vessels", *Lasers Surg. Med.*, 13:219–226 (1993).

Lash et al., "How We Got Here", *Lasers Surg. Med.*, 3:113 (Abstract No. 29) (1983).

Lask et al., "Laser Skin Resurfacing with the SikTouch Flashscanner for Facial Rhytides", *Dermatol. Surg.*, 21:1021–1024 (1995).

Lask et al., "Nonablative laser treatment of facial rhytides", *SPIE*, 2970:338–349 (1997).

Levins et al., "Q–Switched Ruby Laser Treatment of Tattoos", *Lasers Surg Med.*, Suppl. 3:63–64 (Abstract No. 255) (1991).

Lowe et al., "Skin Resurfacing with the Ultrapulse Carbon Dioxide Laser", *Dermatol. Surg.*, 21:1025–1029 (1995).

Magee et al., "Vein Marking Through Ultrasound Coupling Gel", *Eur. J. Vasc. Surg.*, 4:491–492 (1990).

Majaron et al., "Deep Coagulation of Dermal Collagen with Repetitive Er:YAG Laser Irradiation", *Lasers Surg. Med.*, 26:215–222 (2000).

Majaron et al., "Er:YAG Laser Skin Resurfacing Using Repetitive Long–Pulse Exposure and Cryogen Spray Cooling: 1. Histological Study", *Lasers Surg. Med.*, 28:121–130 (2001).

Majaron et al., "Er:YAG Laser Skin Resurfacing Using Repetitive Long–Pulse Exposure and Cryogen Spray Cooling: II. Theoretical Analysis", *Lasers Surg. Med.*, 28:131–137 (2001).

Margolis et al., "Visible Action Spectrum for Melanin–Specific Selective Photothermolysis", *Lasers Surg. Med.*, 9:389–397 (1989).

Marhic et al., "White–Light Flashlamp–pumped dye laser for photography through endoscopes", *Optics Communications*, 45(1):21–25 (1983).

McCaughan et al., "Photodynamic Therapy for Cutaneous and Subcutaneous Malignant Neoplasms", *Arch. Surg.*, 124:211–216 (1989).

McCaughan et al., "Photodynamic Therapy: An Eight–Year Experience", in *Photodynamic Therapy: Basic Principles and Clinical Applications*, pp. 323–331 (1992).

Meijering et al., "Limits of Radial Time Constants to Approximate Thermal Response of Tissue", *Lasers Surg. Med.*, 13:685–687 (1993).

Miller et al., "Optical Modelling of Light Distributions in Skin Tissue Following Laser Irradiation", *Lasers Surg. Med.*, 13:565–571 (1993).

Milner et al., "Analysis of nonablative skin resurfacing", *SPIE*, 2970:367–373 (1997).

Mordon et al., "Rationale for Automatic Scanners in Laser Treatment of Port wine Stains", *Lasers Surg. Med.*, 13:113–123 (1993).

Morelli et al., "Tunable Dye Laser (577 nm) Treatment of Port Wine Stains", *Lasers Surg. Med.*, 6:94–99 (1986).

Motamedi et al., "Thermal Response of Tissue During Laser Angioplasty", *Lasers Surg. Med.*, 5:172 (Abstract No. 114) (1985).

Mutzhas et al., "A New Apparatus with High Radiation Energy Between 320–460 nm: Physical Description and Dermatological Applications", *J. Invest. Dermatol.*, 76:42–47 (1981).

Nakagawa et al., "Ultrastructural Changes in Human Skin After Exposure to a Pulsed Laser", *J. Invest. Dermatol.*, 84(5):396–400 (1985).

Nestor et al., "New Perspectives on Photorejuvenation", *Skin & Aging*, 11:68–74 (2003).

Newman et al., "Variable Pulse Erbium: YAG Laser Skin Resurfacing of Perioral Rhytides and Side–by–side Comparison with Carbon Dioxide Laser", *Lasers Surg. Med.*, 26:208–214 (2000).

Parrish et al., "Exploring Mechanisms of Specificity in Laser–Tissue Interactions", *Lasers Surg. Med.*, 3:175 (Abstract No. 260) (1983).

Parrish et al., "Spatial Confinement of Thermal Effects of Pulsed Laser Irradiation of Tissue", *Lasers Surg. Med.*, 3:157 (Abstract No. 195) (1973).

Paul et al., "The Effect of Temperature and Other Factors on Selective Microvascular Damage Caused by Pulsed Dye Laser", *J. Invest. Dermatol.*, 81(4):333–336 (1983).

Pfefer et al., "Mechanisms of Laser–Induced Thermal Coagulation of Whole Blood in vitro", *SPIE*, 3590:20–31 (1999).

Philipp et al., "Treatment of Congenital Vascular Disorders: Classification, Step Programme and Therapeutical Procedures", *SPIE*, 2086:228–238 (1993).

Pickering et al., "585 nm for the Laser Treatment of Port Wine Stains: A Possible Mechanism", *Lasers Surg. Med.*, 11:616–618 (1991).

Plewig et al., "A new apparatus for the delivery of high intensity UVA and UVA + UVB irradiation, and some dermatological applications", *Br. J. Dermatol.*, 98:15–24 (1978).

Polla et al., "Tunable Pulsed Dye Laser for the Treatment of Benign Cutaneous Vascular Ectasia", *Dermatologica*, 174:11–17 (1987).

Pottier et al., "Assessment of Non–Coherent Light Sources for Photodynamic Therapy", *SPIE*, 2371:364–368 (1995).

Pratesi, R., "Potential Use of Incoherent and Coherent Light–Emitting–Diodes (LEDs) in Photomedicine", in *Photomedicine, Laser Photobiol. Photomed.*, 22:293–308 (1983).

Ramrus et al., "A Compact One–Half MV Rep–Rate Pulser", $20^{th}$ *IEEE Power Modulator Symposium*, pp. 68–71 (1992).

Ramrus et al., "Design and Performance of a One–Half MV Rep–Rate Pulser", Proc. Of the $8^{th}$ IEEE International Pulsed Power Conference, pp. 982–985 (1991).

Ranganathan et al., "Promises for Ultrasonic Waves on Activity of Silica Gel and Some Supported Catalystes", *Ind. Eng. Chem. Prod. Res. Develop.*, 12:155–158 (1973).

Rassing et al., "Measurement of Ultrasonic Absorption in a Gel by Light Diffraction and Resonator Methods", *J. Mol. Liq.*, 26:97–108 (1983).

Rastegar et al., "Technique for Measurement of One–Dimensional Instantaneous Ablation Velocity", *Lasers Surg. Med.*, 8:533–535 (1988).

Raulin et al., "Treatment of a Nonresponding Port–Wine Stain With a New Pulsed Light Source (PhotoDerm® VL)", *Lasers Surg. Med.*, 21:203–208 (1997).

Raulin et al., "Treatment of Adult Port–Wine Stains Using Intense Pulsed Light Therapy (PhotoDerm VL): Brief Initial Clinical Report", *Dermatol. Surg.*, 23:594–601 (1997).

Raulin et al., "Treatment of benign venous malformations with an intense pulsed light source (PhotoDerm VL)", *Eur. J. Dermatol.*, 7:279–282 (1997).

Raulin et al., "Treatment of Essential Telangiectasias with an Intense Pulsed Light Source (PhotoDerm VL)", *Dermatol. Surg.*, 23:941–946 (1997).

Raulin et al., "Treatment of Port–wine Stains With a Noncoherent Pulsed Light Source", *Arch. Dermatol.*, 135:679–683 (1999).

Reyes et al., "Treatment of port–wine stains during childhood with the flashlamp–pumped pulsed dye laser", *J. Am. Acad. Dermatol.*, 23:1142–1148 (1990).

Ross et al., "Effects of $CO_2$ Laser Pulse Duration in Ablation and Residual Thermal Damage: Implications for Skin Resurfacing", *Lasers Surg. Med.*, 19:123–129 (1996).

Rowe, P.M., "Photodynamic therapy begins to shine", *Lancet*, 351:1496 (1998).

Sadick et al., "Photorejuvenation with Intense Pulsed Light: Results of a Multi–Center Study", *J. Drugs Dermatol.*, 3(1):41–49 (2004).

Sadick, N.S., "A Structural Approach to Nonablative Rejuvenation", *Cosmetic Dermatol.*, 15(12):39–43 (2002).

Sadick, N.S., "Update on Non–Ablative Light Therapy for Rejuvenation: A Review", *Lasers Surg. Med.*, 32:120–128 (2003).

Schamiloglu et al., "Modern Pulsed Power: Charlie Martin and Beyond", *Proceedings of the IEEE*, 92(7):1014–1020 (2004).

Schroeter et al., "An Intense Light Source: The Photoderm VL–Flashlamp as a New Treatment Possibility for Vascular Skin Lesions", *Dermatol. Surg.*, 24:743–748 (1998).

Schroeter et al., "Clinical significance of an intense, pulsed light source on leg telangiectasias of up to 1mm diameter", *Eur. J. Dermatol.*, 7:38–42 (1997).

Schroeter et al., "Photoderm VL treatment of leg teleangiectasia", *JEADV*, 5(Suppl. 1):S49 (Abstract No. W76) (1995).

Schwimmer et al., "The Effect of Ultrasound Coupling Gels on Sperm Motility In Vitro", *Fertil. Steril.*, 42:946–947 (1984).

Sheean et al., "Arrest of Embryo Development by Ultrasound Coupling Gels", *Fertil. Steril.*, 45:568–571 (1986).

Smith et al., "532–Nanometer Green Laser Beam Treatment of Superficial Varicosities of the Lower Extremities", *Lasers Surg. Med.*, 8:130–134 (1988).

Steiger et al., "Comparison of Different Pulsed and Q–switched Solid–state Laser Systems for Endoscopic Laser Induced Shock Wave Lithotripsy: Performance and Laser/Stone Interactions", *SPIE*, 2300:94–101 (1990).

Strickland et al., "A 5kV, 250 kA Rep–Rated Pulser Using Parallel Ignitrons", *7th IEEE Int'l Pulsed Conf.*, pp. 729–731 (1989).

Sunde et al., "Traumatic Tattoo Removal: Comparison of Four Treatment Methods in an Animal Model with Correlation to Clinical Experience", *Lasers Surg. Med.*, 10:158–164 (1990).

Svaasand et al., "Light and Drug Distribution with Topically Administered Photosensitizers", *Lasers Surg. Med.*, 11:261–265 (1996).

Szeimies et al., "A Possible New Incoherent Lamp for Photodynamic Treatment of Superficial Skin Lesions", *Acta Derm. Venereol (Stockh).*, 74:117–119 (1994).

Tan et al., "Action Spectrum of Vascular Specific Injury Using Pulsed Irradiation", *J. Invest. Dermatol.*, 92(6):868–871 (1989).

Tan et al., "EMLA for Laser Treatment of Portwine Stains in Children", *Lasers Surg. Med.*, 12:543–548 (1992).

Tan et al., "Histologic Responses of Port–wine Stains Treated by Argon, Carbon Dioxide, and Tunable Dye Lasers", *Arch. Dermatol.*, 122:1016–1022 (1986).

Tan et al., "Pulsed Dye Laser Treatment of Recalcitrant Verrucae: A Preliminary Report", *Lasers Surg. Med.*, 13:127–137 (1993).

Tan et al., "Treatment of Children with Port–Wine Stains Using the Flashlamp–Pulsed Tunable Dye Laser", *N. Engl. J. Med.*, 320(7):416–421 (1989).

Taub, A.F., "Photodynamic Therapy: Other Uses", *Dermtol. Clin.*, 25:101–109 (2007).

Taylor et al., "Q–Switched Ruby laser (QSRL) Irradiation of Benigh Pigmented Lesions: Dermal vs. Epidermal", *Lasers Surg. Med.*, 3:65 (Abstract No. 262) (1991).

Templeton et al., "Comparison of infrared coagulation and rubber band ligation for first and second degree haemorrhoids: a randomized prospective clinical trial", *Br. Med. J.*, 286:1387–1389 (1983).

Troccoli et al., "Multiple–Pulse Photocoagulation of Blood Vessels With A 585 Nm Tunable Laser", *Lasers Surg. Med.*, 4:3 (Abstract No. 2) (1992).

van Gemert et al., "Can Physical Modeling Lead to an Optimal Laser Treatment Strategy for Port Wine Stains", in *Laser Applications in Medicine and Biology*, Chapter 5, pp. 199–247, Plenum Press, New York (1991).

van Germert et al., "Instantaneous Ablation Behavior of In–Vitro Rods During Laser Irradiation", *Lasers Surg. Med.*, 5:136 (Abstract No. 4) (1985).

van Germert et al., "Is There an Optimal Laser Treatment for Port Wine Stains?", *Lasers Surg. Med.*, 6:76–83 (1986).

van Germert et al., "Wavelengths for Laser Treatment of Port Wine Stains and Telangiectasia", *Lasers Surg. Med.*, 16:147–155 (1995).

"Varicose Vein Device Producer comes to U.S. Market", *Clinica*, 687:9 (Jan. 8, 1996).

Venning et al., "Tattoo removal using infra–red coagulation: a dose comparison", *Br. J. Dermatol.*, 117:99–105 (1987).

Wagner et al., "Percutalgine–Gel et Ultrasonotherapie en Pathologie du Sport", *La Revue de Medecine*, 32:1681–1683 (1982) (in French, with English Abstract Only).

Waldorf et al., "Skin Resurfacing of Fine to Deep Rhytides Using a Char–free Carbon Dioxide Laser in 47 Patients", *Dermatol. Surg.*, 21:940–946 (1995).

Walsh et al., "Er:YAG Laser Ablation of Tissue: Measurement of Ablation Rates", *Lasers Surg. Med.*, 9:327–337 (1989).

Walsh et al., "Pulsed $CO_2$ Laser Tissue Ablation: Effect of Tissue Type and Pulse Duration On Thermal Damage", *Lasers Surg. Med.*, 8:108–118 (1988).

Walsh, J.T., "Er:YAG Laser Ablation of Tissue: Effect of Pulse Duration and Tissue Type on Thermal Damage", *Lasers Surg. Med.*, 9:314–316 (1989).

Walsh, J.T., "Pulsed Laser Ablation of Tissue: Analysis of the Removal Process and Tissue Healing", Unpublished Ph.D. dissertation Massachusetts Institute of Tehcnology, on file with Institute Archives and Hayden Library, Massachusetts Institute of Technology, pp. 1–312 (1988).

Weiss et al., "Rejuvenation of Photoaged Skin: 5 Years Results with Intense Pulsed Light of the Face, Neck, and Chest", *Dermatol. Surg.*, 28:1115–1119 (2002).

Welch et al., "Practical Models for Light Distribution in Laser–Irradiated Tissue", *Lasers Surg. Med.*, 6:488–493 (1987).

Werner et al., "Die Hamangiombehandlung mit dem Neodym: Yttrium–Aluminum–Granat Laser (Nd:YAG–Laser)", *Laryngo–Rhino–Otol.*, 71:388–395 (1992), (in German, with English Abstract Only).

West, T., "How Laser Surgery Can Help Your Rosacea Patients", *Skin & Aging*, pp. 43–46 (1998).

Wilder, D., "Pulsed 1064–nm Nd:YAG Laser Therapy for Noninvasive Treatment of a Massive Hemangioma: Case Report", *J. Clin. Laser Med. Surg.*, 17(6):245–247 (1999).

Wilson et al., "The physics of photodynamic therapy", *Phys. Med. Biol.*, 31(4):327–360 (1986).

Walsh et al., *Er–YAG Laser Ablation of Tissue: Measurement of Ablation Rates*, Lasers in Surgery and Medicine, 9:327–337 (1989).

Kaufmann et al., *Pulsed 2.94–ym erbium–YAG laser skin ablation–experimental results and first clinical application*, Clinical and Experimental Dermatology, 15:389–393 (1990).

Walsh et al., *Er–YAG Laser Ablation of Tissue: Effect of Pulse Duration and Tissue Type on Thermal Damage*, Lasers in Surgery and Medicine, 9:314–326 (1989).

Kaufman et al., *Pulsed 2.94–m erbium–YAG laser skin ablation–experimental results and first clinical application*, Clinical and Experimental Dermatology, 15:389–393 (1990).

US 5,964,749 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2 and 5–18 are cancelled.

New claims 19–46 are added and determined to be patentable.

Claims 3 and 4 were not reexamined.

19. *A system for treating a region of skin, the apparatus comprising:*
   *an incoherent pulsed light source disposed in a housing that includes an incoherent light guide that is disposed with respect to the incoherent pulsed light source to direct light emitted from the incoherent light source to the region of skin;*
   *a coherent pulsed light source disposed separate from the housing containing the incoherent pulsed light source and configured to direct light emitted from the coherent pulsed light source to the region of skin using a coherent light guide, wherein the coherent pulsed light source is an Er:YAG laser that is configured to generate light having an intensity and duration sufficient to remove an outer layer of skin; and*
   *an electrical pulse forming network operably connected to either the incoherent or the coherent light sources, the electrical pulse forming network being configured to:*
      *provide electrical pulses to the connected light source;*
      *when coupled to the coherent pulsed light source, provide a delay between sequential pulses of Er:YAG light for a period of time not less than the thermal relaxation time of the skin; and*
      *when coupled to the incoherent pulsed light source, provide pulses of incoherent light that cause collagen in the skin to be heated to a temperature that will shrink the collagen sufficiently to reduce wrinkles.*

20. *The system of claim 19 comprising a microprocessor for controlling the electrical pulse forming network.*

21. *The system of claim 19 wherein the incoherent pulsed light source includes a flashlamp.*

22. *The system of claim 19 further including a filter disposed within the housing and adjacent to the rigid light guide.*

23. *The system of claim 22 wherein the filter is of the type that transmits light having a wavelength in the range of about 550-800 nm.*

24. *The system of claim 19 comprising a cooling material which is disposed on the skin.*

25. *The system of claim 24 wherein the cooling material is a gel.*

26. *An system for treating a region of skin, comprising:*
   *a first treatment head including an incoherent light source and an incoherent light guide, the first treatment head being configured to be put in contact with the skin to direct light from the incoherent light source to the region of skin;*
   *a second treatment head including an Er:YAG laser that is configured to provide pulsed light having an intensity sufficient to remove an outer layer of skin, the second treatment head being configured to direct the coherent light source to the skin; and*
   *an electrical pulse forming network operably connected to either the first or second treatment head, and configured to:*
      *provide electrical pulses to either of the first and second treatment heads such that pulsed light is produced;*
      *when coupled to the first treatment head, provide pulses of incoherent light that cause collagen in the skin to be heated to a temperature that will shrink the collagen sufficiently to reduce wrinkles; and*
      *when coupled to the second treatment head, provide a delay between sequential pulses of Er:YAG light for a period of time not less than the thermal relaxation time of the skin.*

27. *The system of claim 26 wherein the incoherent light source is a flashlamp.*

28. *The system of claim 27 comprising a simmer power supply configured to keep the flashlamp in a low current conducting mode.*

29. *The system of claim 26 comprising a microprocessor configured to provide control signals to the pulse forming network.*

30. *The system of claim 26 wherein the pulse forming network is configured to provide a train of pulses to either the coherent or incoherent light source.*

31. *A system for skin rejuvenation by removing at least an outer layer of skin in a region of skin comprising:*
   *an incoherent light source disposed in a housing including a light guide capable of contacting the region of skin and directing light to the region of skin for a duration and with an intensity sufficient to heat collagen in the skin to a temperature sufficient to reduce wrinkling;*
   *an Er:YAG laser light source disposed separate from the housing and capable of directing pulses of light to at least a portion of the region of skin for a duration and with an intensity sufficient to remove the outer layer of that portion of skin;*
   *a pulse forming circuit coupled to either the incoherent light source or the Er:YAG laser light source and configured to provide electrical pulses to either of the light sources; and*
   *a microprocessor operably coupled to the pulse forming circuit and configured for controlling the pulse durations of the electrical pulses.*

32. *The apparatus of claim 31 wherein the pulse forming circuit produces a train of pulses.*

33. *The apparatus of claim 31 wherein the Er:YAG laser is pumped by a flashlamp.*

34. *An apparatus for the cutaneous resurfacing of a region of skin, including skin resurfacing and wrinkle smoothing, which comprises:*
   *an incoherent pulsed light source such as a flashlamp, disposed in a housing, the incoherent pulsed light source for generating incoherent light for heating collagen to a temperature sufficient to reduce wrinkling;* a coherent pulsed light source disposed separate from the housing and configured to direct light emitted from the coherent pulsed light source to the region of skin, wherein the coherent pulsed light source is a Er:YAG laser which can be operated in multiple pulse mode for generating laser light; and a delivery system disposed to deliver the incoherent light and laser light to the region of skin, wherein the delivery system includes at least a rigid light guide that is disposed in the housing with respect to the incoherent pulsed light source to direct light emitted from the incoherent pulsed light source to the region of skin; and an electrical pulse forming network configured to operably connect to either the incoherent pulsed light source or to the coherent pulsed light source, and configured to provide electrical pulses to the connected light source.

35. The apparatus of claim 34 further comprising a microprocessor for controlling a pulse duration of the electrical pulses.

36. The apparatus of claim 34 further comprising a filter disposed within the housing and adjacent to the rigid light guide.

37. The apparatus of claim 36 wherein the filter is of the type that transmits light having a wavelength in the range of about 550-800 nm.

38. The apparatus of claim 34 further comprising a cooling material which is disposed on the region of skin.

39. The apparatus of claim 38 wherein the cooling material is a gel.

40. An apparatus for skin rejuvenation by removing at least an outer layer of skin in a region of skin comprising:

a coherent pulsed Er:YAG laser light source disposed in a first housing capable of directing light to the region of skin for a duration and with an intensity sufficient to remove the outer layer;

an incoherent pulsed light source disposed in a second housing that includes a rigid light guide that is disposed with respect the incoherent pulsed light source to direct light emitted from the incoherent light source to the region of skin;

an electrical pulse forming circuit coupled to the Er:YAG laser light source including a pulse delay circuit for providing a delay between sequential pulses of Er:YAG light for a period of time not less than the thermal relaxation time of the skin, wherein the electrical pulse forming circuit is also configured to couple to the incoherent light source to provide electrical pulses to the incoherent light source.

41. The apparatus of claim 40 further comprising a microprocessor for controlling the pulse duration of the electrical pulses.

42. The apparatus of claim 40 wherein the incoherent pulsed light source is a flashlamp.

43. The apparatus of claim 40 further comprising a filter disposed within the second housing and adjacent to the rigid light guide.

44. The apparatus of claim 43 wherein the filter is of the type that transmits light having a wavelength of about 550-800 nm.

45. The apparatus of claim 40 further comprising a cooling material which is disposed on the skin.

46. The apparatus of claim 45 wherein the cooling material is a gel.

* * * * *

(12) EX PARTE REEXAMINATION CERTIFICATE (7383rd)
United States Patent
Eckhouse et al.

(10) Number: US 5,964,749 C2
(45) Certificate Issued: Feb. 23, 2010

(54) METHOD AND APPARATUS FOR SKIN REJUVENATION AND WRINKLE SMOOTHING

(75) Inventors: Shimon Eckhouse, Haifa (IL); Michael Kreindel, Haifa (IL)

(73) Assignee: Lumenis Ltd., Yokneam (IL)

Reexamination Request:
No. 90/010,388, Apr. 14, 2009

Reexamination Certificate for:
Patent No.: 5,964,749
Issued: Oct. 12, 1999
Appl. No.: 08/529,044
Filed: Sep. 15, 1995

Reexamination Certificate C1 5,964,749 issued Mar. 31, 2009

(51) Int. Cl.
*A61N 5/06* (2006.01)

(52) U.S. Cl. ............................................. 606/9; 607/88
(58) Field of Classification Search ........................ None
See application file for complete search history.

(56) References Cited

U.S. PATENT DOCUMENTS

| | | | |
|---|---|---|---|
| 1,106,699 A | 8/1914 | Carroll | 600/200 |
| 1,651,385 A | 12/1927 | Goodrich | 392/409 |
| 2,699,771 A | 1/1955 | Ruttger-Pelli | 601/15 |
| 2,716,698 A | 8/1955 | Brukner | 240/1 |
| 2,888,927 A | 6/1959 | Fozard | 606/43 |
| 2,954,771 A | 10/1960 | Boyan | 128/396 |
| 3,126,295 A | 3/1964 | Young | 428/337 |
| 3,289,669 A | 12/1966 | Dwyer et al. | 600/565 |
| 3,307,553 A | 3/1967 | Liebner | 607/1 |
| 3,327,712 A | 6/1967 | Kaufman et al. | 606/40 |
| 3,538,919 A | 11/1970 | Meyer | 606/36 |
| 3,559,531 A | 2/1971 | Leibfritz et al. | 91/26 |
| 3,599,934 A | 8/1971 | Reed | 251/363 |
| 3,601,616 A | 8/1971 | Katsumata | 250/223 |

(Continued)

FOREIGN PATENT DOCUMENTS

| | | |
|---|---|---|
| AT | 355200 | 3/2006 |
| AU | 1851583 | 3/1984 |
| AU | 2940397 | 12/1997 |

(Continued)

OTHER PUBLICATIONS

"Sharplan 771 Microscan Data Sheet", Mar. 28, 1985.
Alster et al., "Improvement of facial acne scars by the 585 nm flashlamp-pumped pulsed dye laser", *Journal of the American Academy of Dermatology*, 35(1):79–81 (Jul. 1996).
Alster et al., "Treatment of Scars: A Review", *Annuals of Plastic Surgery*, 39(4):418–432 (Oct. 1997).

(Continued)

*Primary Examiner*—Beverly M. Flanagan

(57) ABSTRACT

A method and apparatus for treating skin includes applying pulsed light to the skin to heat and shrinking collagen within the skin, thereby reviving the elasticity of the collagen and of the skin. The epidermis and outer layers of the skin may be protected by cooling with a transparent substance, such as ice or gel to the skin. The temperature distribution within the skin is controlled by controlling the delay between the time the coolant is applied, and the time the light is applied, by controlling the pulse duration and applying multiple pulses, and by filtering the light and controlling the radiation spectrum, preferably, the spectrum includes light having a wavelength in the range of 600-1200 nm. The pulsed light may be incoherent, such as that produced by a flashlamp, or coherent, such as that produced by a Nd(Yag) laser or a ruby laser, and may be directed to the skin using a flexible or rigid light guide. Also, a method and apparatus for cutaneous resurfacing including directing Er:YAG laser light to the skin. The light may be pulsed, preferably with a delay of about 0.5-10 msec between pulses. In one embodiment the pulses have energy fluences of preferably about 100 J/cm$^2$.

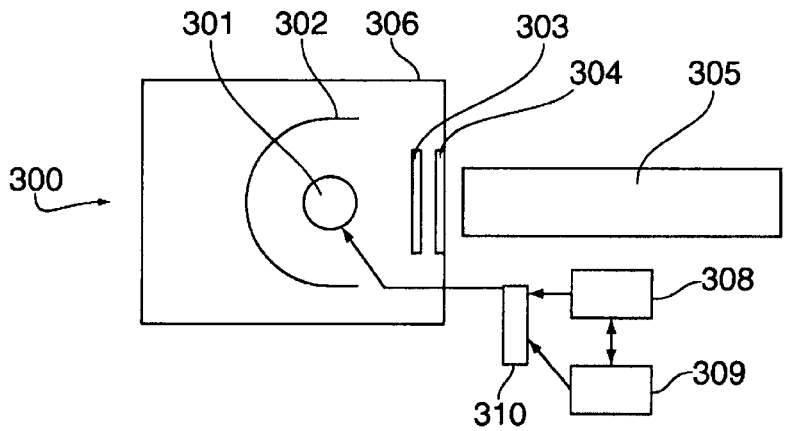

U.S. PATENT DOCUMENTS

| | | | |
|---|---|---|---|
| 3,658,068 A | 4/1972 | McNall | 128/395 |
| 3,680,000 A | 7/1972 | Chester et al. | 372/99 |
| 3,693,623 A | 9/1972 | Harte et al. | 606/9 |
| 3,710,798 A | 1/1973 | Bredemeier | 606/11 |
| 3,804,732 A | 4/1974 | Goodkin | 204/58 |
| 3,806,829 A | 4/1974 | Duston et al. | 372/38.01 |
| 3,818,914 A | 6/1974 | Bender | 607/90 |
| 3,821,510 A | 6/1974 | Muncheryan | 219/121 |
| 3,834,391 A | 9/1974 | Block | 606/9 |
| 3,884,236 A | 5/1975 | Krasnov | 606/3 |
| 3,916,143 A | 10/1975 | Farrell | 219/121.69 |
| 3,930,504 A | 1/1976 | de Laforcade | 128/303.1 |
| 3,967,627 A | 7/1976 | Brown | 128/400 |
| 3,999,552 A | 12/1976 | Huggins | 128/303.13 |
| 4,022,534 A | 5/1977 | Kishner | 356/446 |
| 4,058,752 A | 11/1977 | Woods et al. | 315/360 |
| 4,112,335 A | 9/1978 | Gonser | 315/241 R |
| 4,122,853 A | 10/1978 | Smith | 606/4 |
| 4,174,714 A | 11/1979 | Mehl | 128/303.13 |
| 4,213,462 A | 7/1980 | Sato | 128/634 |
| 4,229,658 A | 10/1980 | Gonser | 250/504 H |
| 4,232,678 A | 11/1980 | Skovajsa | 128/395 |
| 4,233,493 A | 11/1980 | Nath | 219/354 |
| 4,241,382 A | 12/1980 | Daniel | 362/581 |
| 4,246,902 A | 1/1981 | Martinez | 604/22 |
| 4,266,548 A | 5/1981 | Davi | 606/14 |
| 4,283,661 A | 8/1981 | Doty | 315/360 |
| 4,298,005 A | 11/1981 | Mutzhas | 128/396 |
| 4,316,467 A | 2/1982 | Muckerheide | 606/9 |
| 4,321,930 A | 3/1982 | Jobsis et al. | 128/633 |
| 4,336,809 A | 6/1982 | Clark | 128/665 |
| 4,366,570 A | 12/1982 | Bees | 372/70 |
| 4,380,240 A | 4/1983 | Jobsis et al. | 128/633 |
| 4,381,007 A | 4/1983 | Doss | 128/303.1 |
| 4,387,952 A | 6/1983 | Slusher | 359/220.1 |
| 4,388,924 A | 6/1983 | Weissman et al. | 128/303.1 |
| 4,408,602 A | 10/1983 | Nakajima | 606/10 |
| 4,436,097 A | 3/1984 | Cunningham | 600/520 |
| 4,441,485 A | 4/1984 | Reynolds | 600/200 |
| 4,444,190 A | 4/1984 | Mutzhas | 128/396 |
| 4,454,882 A | 6/1984 | Takano | 607/89 |
| 4,469,098 A | 9/1984 | Davi | 605/7 |
| 4,497,018 A | 1/1985 | Rice | 363/96 |
| 4,503,854 A | 3/1985 | Jako | 606/11 |
| 4,506,196 A | 3/1985 | Bees | 315/241 R |
| 4,515,165 A | 5/1985 | Carroll | 600/475 |
| 4,516,195 A | 5/1985 | Gonser | 362/281 |
| 4,520,816 A | 6/1985 | Schachar et al. | 606/4 |
| 4,521,194 A | 6/1985 | Myers et al. | 433/215 |
| 4,539,987 A | 9/1985 | Nath et al. | 128/303.1 |
| 4,554,666 A | 11/1985 | Altman | 372/19 |
| 4,555,179 A | 11/1985 | Langerholc et al. | 356/342 |
| 4,559,942 A | 12/1985 | Eisenberg | 128/303 |
| 4,560,883 A | 12/1985 | Kerschgens | 250/504 |
| 4,564,011 A | 1/1986 | Goldman | 128/303.1 |
| 4,566,453 A | 1/1986 | Kumano et al. | 606/8 |
| 4,587,396 A | 5/1986 | Rubin | 219/121.78 |
| 4,601,037 A | 7/1986 | McDonald | 372/25 |
| 4,608,978 A | 9/1986 | Rohr | 606/9 |
| 4,608,979 A | 9/1986 | Breidenthal et al. | 128/303.1 |
| 4,611,245 A | 9/1986 | Trias et al. | 358/235 |
| 4,617,926 A | 10/1986 | Sutton | 606/9 |
| 4,619,887 A | 10/1986 | Hooper et al. | 430/313 |
| 4,620,547 A | 11/1986 | Boebel | 600/567 |
| 4,645,980 A | 2/1987 | Yang | 315/159 |
| 4,647,830 A | 3/1987 | Bees | 320/1 |
| 4,653,495 A | 3/1987 | Nanaumi | 128/303.1 |
| 4,657,018 A | 4/1987 | Hakky | 606/46 |
| 4,669,466 A | 6/1987 | L'Esperance | 606/3 |
| 4,672,969 A | 6/1987 | Dew | 128/397 |
| 4,686,986 A | 8/1987 | Fenyo et al. | 607/90 |
| 4,712,537 A | 12/1987 | Pender | 600/200 |
| 4,718,418 A | 1/1988 | L'Esperance, Jr. | 606/5 |
| 4,726,377 A | 2/1988 | Jegers et al. | 128/376 |
| 4,729,375 A | 3/1988 | Jegers et al. | 128/376 |
| 4,733,660 A | 3/1988 | Itzkan | 128/303.1 |
| 4,744,360 A | 5/1988 | Bath | 606/6 |
| 4,750,486 A | 6/1988 | Butler et al. | 606/18 |
| 4,754,381 A | 6/1988 | Downs | 362/297 |
| 4,757,431 A | 7/1988 | Cross et al. | 362/261 |
| 4,768,513 A | 9/1988 | Suzuki | 600/476 |
| 4,773,097 A | 9/1988 | Suzaki et al. | 382/128 |
| 4,775,361 A | 10/1988 | Jacques et al. | 604/20 |
| 4,784,135 A | 11/1988 | Blum et al. | 606/3 |
| 4,792,341 A | 12/1988 | Kozikowski et al. | 8/103 |
| 4,803,694 A | 2/1989 | Lee et al. | 372/98 |
| 4,810,658 A | 3/1989 | Shanks et al. | 436/172 |
| 4,818,230 A | 4/1989 | Myers et al. | 433/215 |
| 4,818,847 A | 4/1989 | Hara et al. | 235/455 |
| 4,829,262 A | 5/1989 | Furumoto | 330/4.3 |
| 4,835,749 A | 5/1989 | Welton | 368/10 |
| 4,839,562 A | 6/1989 | Francis et al. | 315/149 |
| 4,840,798 A | 6/1989 | Skaliotis | 424/488 |
| 4,846,172 A | 7/1989 | Berlin | 606/4 |
| 4,846,192 A | 7/1989 | MacDonald | 600/565 |
| 4,851,738 A | 7/1989 | Yang | 315/159 |
| 4,858,090 A | 8/1989 | Downs | 362/297 |
| 4,860,172 A | 8/1989 | Schlager et al. | 362/553 |
| 4,862,886 A | 9/1989 | Clarke et al. | 606/7 |
| 4,871,559 A | 10/1989 | Dunn et al. | 426/248 |
| 4,874,009 A | 10/1989 | Pickerrell et al. | 137/454.6 |
| 4,874,361 A | 10/1989 | Obagi | 606/3 |
| 4,875,214 A | 10/1989 | Denne | 372/5 |
| 4,883,333 A | 11/1989 | Yanez | 385/33 |
| 4,884,568 A | 12/1989 | Hahn | 128/303.1 |
| 4,894,547 A | 1/1990 | Leffell et al. | 250/461.2 |
| 4,897,771 A | 1/1990 | Parker | 362/298 |
| 4,907,235 A | 3/1990 | Kuizenga | 372/21 |
| 4,909,782 A | 3/1990 | Semm et al. | 606/171 |
| 4,910,942 A | 3/1990 | Dunn | 53/425 |
| 4,913,132 A | 4/1990 | Gabriel | 600/200 |
| 4,917,083 A | 4/1990 | Harrington et al. | 606/15 |
| 4,917,084 A | 4/1990 | Sinofsky | 606/7 |
| 4,917,486 A | 4/1990 | Raven et al. | 351/221 |
| 4,926,861 A | 5/1990 | Fenyo et al. | 607/88 |
| 4,930,504 A | 6/1990 | Diamantopoulos et al. | 128/395 |
| 4,938,221 A | 7/1990 | Tuffel | 128/401 |
| 4,940,922 A | 7/1990 | Schuda et al. | 315/246 |
| 4,941,082 A | 7/1990 | Pailthorp et al. | 700/57 |
| 4,945,914 A | 8/1990 | Allen | 600/426 |
| 4,947,305 A | 8/1990 | Gunter, Jr. | 362/297 |
| 4,947,859 A | 8/1990 | Brewer et al. | 128/715 |
| 4,950,880 A | 8/1990 | Hayner | 250/201.9 |
| 4,955,882 A | 9/1990 | Hakky | 605/14 |
| 4,973,848 A | 11/1990 | Kolobanov et al. | 250/458.1 |
| 4,974,138 A | 11/1990 | Negishi | 362/347 |
| 4,976,709 A | 12/1990 | Sand | 606/5 |
| 4,988,163 A | 1/1991 | Cohen et al. | 385/31 |
| 4,996,046 A | 2/1991 | Warshaw et al. | 424/445 |
| 5,000,752 A | 3/1991 | Hoskin et al. | 606/9 |
| 5,005,180 A | 4/1991 | Edelman et al. | 372/57 |
| 5,008,579 A | 4/1991 | Conley et al. | 310/303 |
| 5,011,793 A | 4/1991 | Obinata | 427/383.1 |
| 5,016,151 A | 5/1991 | Mula | 362/267 |
| 5,020,995 A | 6/1991 | Levy | 433/215 |
| 5,023,886 A | 6/1991 | Hobart et al. | 372/99 |
| 5,025,446 A | 6/1991 | Kuizenga | 372/21 |
| 5,034,235 A | 7/1991 | Dunn et al. | 426/238 |
| 5,039,867 A | 8/1991 | Nishihara et al. | 250/492.3 |
| 5,048,034 A | 9/1991 | Tulip | 372/41 |
| 5,049,147 A | 9/1991 | Danon | 606/10 |

| Patent No. | Date | Inventor | Class |
|---|---|---|---|
| 5,054,488 A | 10/1991 | Muz | 128/633 |
| 5,057,100 A | 10/1991 | Lombardo | 606/17 |
| 5,057,104 A | 10/1991 | Chess | 606/9 |
| 5,059,192 A | 10/1991 | Zaias | 606/9 |
| 5,063,961 A | 11/1991 | Brunner | 137/454.5 |
| 5,066,291 A | 11/1991 | Stewart | 606/3 |
| 5,066,293 A | 11/1991 | Furumoto | 606/9 |
| 5,071,417 A | 12/1991 | Sinofsky | 606/8 |
| 5,071,422 A | 12/1991 | Watson et al. | 606/128 |
| 5,074,861 A | 12/1991 | Schneider et al. | 606/17 |
| 5,077,099 A | 12/1991 | Kukanskis et al. | 427/437 |
| 5,078,711 A | 1/1992 | Kakami et al. | 606/16 |
| 5,083,093 A | 1/1992 | Adler et al. | 328/65 |
| 5,084,881 A | 1/1992 | Farries et al. | 372/6 |
| 5,089,945 A | 2/1992 | Mula | 362/261 |
| 5,097,471 A | 3/1992 | Negus et al. | 372/18 |
| 5,106,364 A | 4/1992 | Hayafuji et al. | 604/22 |
| 5,109,463 A | 4/1992 | Lee | 385/123 |
| 5,112,328 A | 5/1992 | Taboada et al. | 606/4 |
| 5,113,462 A | 5/1992 | Clancy et al. | 385/53 |
| 5,123,026 A | 6/1992 | Fan et al. | 372/75 |
| 5,125,922 A | 6/1992 | Dwyer et al. | 606/3 |
| 5,126,621 A | 6/1992 | Morton et al. | 313/237 |
| 5,130,997 A | 7/1992 | Ortiz et al. | 372/21 |
| 5,133,035 A | 7/1992 | Hicks | 385/117 |
| 5,137,539 A | 8/1992 | Bowling | 44/626 |
| 5,139,494 A | 8/1992 | Freiberg | 606/3 |
| 5,146,923 A | 9/1992 | Dhawan | 600/476 |
| 5,161,526 A | 11/1992 | Hellwing et al. | 607/89 |
| 5,178,617 A | 1/1993 | Kuizenga et al. | 606/17 |
| 5,194,723 A | 3/1993 | Cates et al. | 250/205 |
| 5,200,604 A | 4/1993 | Rudko et al. | 250/205 |
| 5,201,731 A | 4/1993 | Hakky | 606/15 |
| 5,204,517 A | 4/1993 | Cates et al. | 250/205 |
| 5,206,867 A | 4/1993 | Esterowitz et al. | 372/20 |
| 5,207,670 A | 5/1993 | Sinofsky | 606/8 |
| 5,207,671 A | 5/1993 | Franken et al. | 606/9 |
| 5,217,455 A | 6/1993 | Tan | 606/9 |
| 5,222,952 A | 6/1993 | Loertscher | 606/6 |
| 5,226,107 A | 7/1993 | Stern et al. | 392/416 |
| 5,226,430 A | 7/1993 | Spears et al. | 128/898 |
| 5,226,907 A | 7/1993 | Tankovich | 606/133 |
| 5,242,460 A | 9/1993 | Klein et al. | 606/159 |
| 5,243,615 A | 9/1993 | Ortiz et al. | 372/34 |
| 5,246,435 A | 9/1993 | Bille et al. | 606/6 |
| 5,246,436 A | 9/1993 | Rowe | 606/13 |
| 5,247,935 A | 9/1993 | Cline et al. | 128/653.2 |
| 5,249,190 A | 9/1993 | Kortz et al. | 372/22 |
| 5,257,274 A | 10/1993 | Barrett et al. | 372/20 |
| 5,259,380 A | 11/1993 | Mendes et al. | 607/115 |
| 5,263,038 A | 11/1993 | Lukas et al. | 372/22 |
| 5,263,950 A | 11/1993 | L'Esperance, Jr. | 606/6 |
| 5,265,598 A | 11/1993 | Searfoss et al. | 607/88 |
| 5,269,778 A | 12/1993 | Rink et al. | 606/12 |
| 5,272,518 A | 12/1993 | Vincent | 356/405 |
| 5,272,713 A | 12/1993 | Sobey et al. | 372/69 |
| 5,274,728 A | 12/1993 | Tran | 385/142 |
| 5,280,378 A | 1/1994 | Lombardo | 359/199.1 |
| 5,281,798 A | 1/1994 | Hamm et al. | 250/205 |
| 5,282,797 A | 2/1994 | Chess | 606/9 |
| 5,282,798 A | 2/1994 | Bruse et al. | 606/17 |
| 5,287,380 A | 2/1994 | Hsia | 372/69 |
| 5,289,479 A | 2/1994 | Oka et al. | 372/22 |
| 5,290,273 A | 3/1994 | Tan | 606/9 |
| 5,290,274 A | 3/1994 | Levy et al. | 606/13 |
| 5,293,872 A | 3/1994 | Alfano | 128/664 |
| 5,300,097 A | 4/1994 | Lerner et al. | 607/93 |
| 5,304,167 A | 4/1994 | Freiberg | 606/3 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,312,396 A | 5/1994 | Feld et al. | 606/11 |
| 5,312,399 A | 5/1994 | Hakky et al. | 606/15 |
| 5,320,618 A | 6/1994 | Gustafsson | 606/9 |
| 5,321,715 A | 6/1994 | Trost | 372/69 |
| 5,325,458 A | 6/1994 | Morrow et al. | 385/125 |
| 5,328,488 A | 7/1994 | Daikuzono | 606/16 |
| 5,328,517 A | 7/1994 | Cates et al. | 134/7 |
| 5,330,517 A | 7/1994 | Mordon et al. | 607/89 |
| 5,334,190 A | 8/1994 | Seiler | 606/5 |
| 5,336,216 A | 8/1994 | Dewey | 606/4 |
| 5,336,217 A | 8/1994 | Buys et al. | 606/9 |
| 5,337,741 A | 8/1994 | Diamond | 600/8 |
| 5,342,198 A | 8/1994 | Vassiliadis et al. | 433/215 |
| 5,344,418 A | 9/1994 | Ghaffari | 606/9 |
| 5,344,433 A | 9/1994 | Talmore | 607/88 |
| 5,344,434 A | 9/1994 | Talmore | 607/88 |
| 5,345,457 A | 9/1994 | Zenzie et al. | 372/22 |
| 5,349,590 A | 9/1994 | Amirkhanian et al. | 372/6 |
| 5,360,424 A | 11/1994 | Klopotek | 606/4 |
| 5,363,387 A | 11/1994 | Sinofsky | 372/15 |
| 5,363,854 A | 11/1994 | Martens et al. | 600/477 |
| 5,364,390 A | 11/1994 | Taboada et al. | 606/10 |
| 5,368,031 A | 11/1994 | Cline et al. | 600/411 |
| 5,368,634 A | 11/1994 | Hackett | 95/260 |
| 5,370,651 A | 12/1994 | Summers | 606/159 |
| 5,374,265 A | 12/1994 | Sand | 606/5 |
| 5,375,132 A | 12/1994 | Connors et al. | 372/34 |
| 5,382,013 A | 1/1995 | Walsh | 271/186 |
| 5,383,467 A | 1/1995 | Auer | 128/664 |
| 5,384,796 A | 1/1995 | Jee | 372/22 |
| 5,386,837 A | 2/1995 | Sterzer | 128/898 |
| 5,387,211 A | 2/1995 | Saadatmanesh et al. | 606/10 |
| 5,390,204 A | 2/1995 | Yessik | 372/38 |
| 5,394,307 A | 2/1995 | Matsuura | 362/16 |
| 5,395,362 A | 3/1995 | Sacharoff et al. | 606/17 |
| 5,397,327 A | 3/1995 | Koop et al. | 606/17 |
| 5,400,428 A | 3/1995 | Grace | 385/115 |
| 5,400,791 A | 3/1995 | Schlier et al. | 128/664 |
| 5,401,171 A | 3/1995 | Paghdiwala | 433/215 |
| 5,403,276 A | 4/1995 | Schechter et al. | 604/22 |
| 5,405,368 A | 4/1995 | Eckhouse | 607/88 |
| 5,405,726 A | 4/1995 | Abe et al. | 430/97 |
| 5,406,577 A | 4/1995 | Gagosz | 372/69 |
| 5,409,479 A | 4/1995 | Dew et al. | 606/9 |
| 5,409,483 A | 4/1995 | Campbell et al. | 606/15 |
| 5,411,502 A | 5/1995 | Zair | 606/10 |
| 5,414,600 A | 5/1995 | Strobl et al. | 362/551 |
| 5,422,899 A | 6/1995 | Freiberg et al. | 372/25 |
| 5,423,798 A | 6/1995 | Crow | 606/4 |
| 5,423,803 A | 6/1995 | Tankovich et al. | 606/9 |
| 5,425,728 A | 6/1995 | Tankovich | 606/9 |
| 5,431,646 A | 7/1995 | Vassiliadis et al. | 606/6 |
| 5,435,724 A | 7/1995 | Goodman et al. | 433/215 |
| 5,438,303 A | 8/1995 | Murakami et al. | 332/109 |
| 5,441,531 A | 8/1995 | Zarate et al. | |
| 5,445,146 A | 8/1995 | Bellinger | 607/89 |
| D363,349 S | 10/1995 | Dittert | D24/158 |
| 5,454,807 A | 10/1995 | Lennox et al. | 606/15 |
| 5,456,689 A | 10/1995 | Kresch et al. | 606/180 |
| 5,458,112 A | 10/1995 | Weaver | 600/566 |
| 5,474,528 A | 12/1995 | Meserol | 604/20 |
| 5,474,549 A | 12/1995 | Ortiz et al. | 606/9 |
| 5,476,461 A | 12/1995 | Cho et al. | 606/15 |
| 5,484,432 A | 1/1996 | Sand | 606/5 |
| 5,489,279 A | 2/1996 | Meserol | 604/290 |
| 5,490,860 A | 2/1996 | Middle et al. | 606/171 |
| 5,498,258 A | 3/1996 | Hakky et al. | 606/15 |
| 5,498,935 A | 3/1996 | McMahan et al. | 315/241 P |
| 5,501,680 A | 3/1996 | Kurtz et al. | 606/9 |
| 5,511,563 A | 4/1996 | Diamond | 128/898 |
| 5,520,679 A | 5/1996 | Lin | 606/5 |

| Patent No. | Date | Inventor | Class |
|---|---|---|---|
| 5,522,814 A | 6/1996 | Bernaz | 606/36 |
| 5,527,332 A | 6/1996 | Clement | 606/171 |
| 5,527,350 A | 6/1996 | Grove et al. | 607/89 |
| 5,529,954 A | 6/1996 | Iijima et al. | 438/653 |
| 5,531,739 A | 7/1996 | Trelles | 606/2.5 |
| 5,531,740 A | 7/1996 | Black | 606/9 |
| 5,540,676 A | 7/1996 | Freiberg | 606/3 |
| 5,544,651 A | 8/1996 | Wilk | 600/310 |
| 5,546,214 A | 8/1996 | Black et al. | 359/203 |
| 5,558,666 A | 9/1996 | Dewey et al. | 606/9 |
| 5,558,667 A | 9/1996 | Yarborough et al. | 606/9 |
| 5,560,699 A | 10/1996 | Davenport et al. | 362/558 |
| 5,569,284 A | 10/1996 | Young et al. | 606/180 |
| 5,572,311 A | 11/1996 | Abe | 399/127 |
| 5,578,029 A | 11/1996 | Trelles et al. | 606/25 |
| 5,586,981 A | 12/1996 | Hu | 606/9 |
| 5,588,428 A | 12/1996 | Smith et al. | 600/425 |
| 5,591,157 A | 1/1997 | Hennings et al. | 606/3 |
| 5,595,568 A | 1/1997 | Anderson et al. | 606/9 |
| 5,599,342 A | 2/1997 | Hsia et al. | 606/9 |
| 5,606,798 A | 3/1997 | Kelman | 30/41.5 |
| 5,608,520 A | 3/1997 | Fleming | 356/318 |
| 5,611,795 A | 3/1997 | Slatkine et al. | 606/9 |
| 5,618,284 A | 4/1997 | Sand | 606/5 |
| 5,618,285 A | 4/1997 | Zair | 606/10 |
| 5,620,478 A | 4/1997 | Eckhouse | 607/88 |
| 5,621,745 A | 4/1997 | Yessik et al. | 372/26 |
| 5,626,631 A | 5/1997 | Eckhouse | 607/88 |
| 5,628,744 A | 5/1997 | Coleman et al. | 606/12 |
| 5,630,811 A | 5/1997 | Miller | 606/9 |
| 5,642,370 A | 6/1997 | Mitchell et al. | 372/25 |
| 5,643,334 A | 7/1997 | Eckhouse et al. | 697/88 |
| 5,644,585 A | 7/1997 | Mitchell et al. | 372/25 |
| 5,649,972 A | 7/1997 | Hochstein | 607/100 |
| 5,655,547 A | 8/1997 | Karni | 128/898 |
| 5,658,323 A | 8/1997 | Miller | 607/89 |
| 5,660,836 A | 8/1997 | Knowlton | 424/400 |
| 5,662,644 A | 9/1997 | Swor | 606/9 |
| 5,683,380 A | 11/1997 | Eckhouse et al. | 606/9 |
| 5,707,413 A | 1/1998 | Inao | 65/78 |
| 5,710,626 A | 1/1998 | O'rourke et al. | 356/301 |
| 5,720,772 A | 2/1998 | Eckhouse | 607/88 |
| 5,722,970 A | 3/1998 | Colvard et al. | 606/3 |
| 5,725,565 A | 3/1998 | Smith | 607/88 |
| 5,733,277 A | 3/1998 | Pallarito | 606/7 |
| 5,733,297 A | 3/1998 | Wang | 606/167 |
| 5,735,844 A | 4/1998 | Anderson et al. | 606/9 |
| 5,738,677 A | 4/1998 | Colvard et al. | 606/4 |
| 5,741,245 A | 4/1998 | Cozean et al. | 606/5 |
| 5,743,902 A | 4/1998 | Trost | 606/18 |
| 5,748,655 A | 5/1998 | Yessik et al. | 372/22 |
| 5,749,868 A | 5/1998 | Furumoto | 606/9 |
| 5,754,573 A | 5/1998 | Yarborough et al. | 372/22 |
| 5,755,751 A | 5/1998 | Eckhouse | 607/88 |
| 5,755,753 A | 5/1998 | Knowlton | 607/98 |
| 5,769,844 A | 6/1998 | Ghaffari | 606/16 |
| 5,776,175 A | 7/1998 | Eckhouse et al. | 607/100 |
| 5,783,798 A | 7/1998 | Abraham | 219/121.73 |
| 5,786,929 A | 7/1998 | Nabors | 359/330 |
| 5,810,801 A | 9/1998 | Anderson et al. | 606/9 |
| 5,814,040 A | 9/1998 | Nelson et al. | 606/9 |
| 5,817,089 A | 10/1998 | Tankovich et al. | 606/9 |
| 5,817,090 A | 10/1998 | Abergel et al. | 606/9 |
| 5,828,803 A | 10/1998 | Eckhouse | 385/88 |
| 5,830,208 A | 11/1998 | Muller | 606/9 |
| 5,833,612 A | 11/1998 | Eckhouse et al. | 600/476 |
| 5,833,683 A | 11/1998 | Fuller et al. | 606/17 |
| 5,836,939 A | 11/1998 | Negus et al. | 606/11 |
| 5,836,999 A | 11/1998 | Eckhouse et al. | 607/88 |
| 5,843,143 A | 12/1998 | Whitehurst | 607/88 |
| 5,849,029 A | 12/1998 | Eckhouse et al. | 607/104 |
| 5,853,407 A | 12/1998 | Miller | 606/9 |
| 5,855,595 A | 1/1999 | Fujishima et al. | 607/90 |
| 5,860,967 A | 1/1999 | Zavislan et al. | 605/9 |
| 5,860,968 A | 1/1999 | Wojcik et al. | 606/10 |
| 5,865,830 A | 2/1999 | Parel et al. | 606/5 |
| 5,871,479 A | 2/1999 | Furumoto et al. | 606/9 |
| 5,879,346 A | 3/1999 | Waldman et al. | 606/9 |
| 5,879,376 A | 3/1999 | Miller | 607/89 |
| 5,885,273 A | 3/1999 | Eckhouse et al. | 606/9 |
| 5,885,274 A | 3/1999 | Fullmer | 606/9 |
| 5,900,211 A | 5/1999 | Dunn et al. | 422/24 |
| 5,906,609 A | 5/1999 | Assa et al. | 606/9 |
| 5,907,574 A | 5/1999 | Karni | 372/95 |
| 5,911,718 A | 6/1999 | Yarborough et al. | 606/9 |
| 5,912,457 A | 6/1999 | McQuaid | 240/227.17 |
| 5,938,657 A | 8/1999 | Assa et al. | 606/9 |
| 5,957,915 A | 9/1999 | Trost | 606/13 |
| 5,970,983 A | 10/1999 | Karni et al. | 128/898 |
| 5,983,900 A | 11/1999 | Clement et al. | 128/898 |
| 6,024,751 A | 2/2000 | Lovato et al. | 606/170 |
| RE36,634 E | 3/2000 | Ghaffari | 606/9 |
| 6,045,548 A | 4/2000 | Furumoto et al. | 606/9 |
| 6,077,294 A | 6/2000 | Cho et al. | 607/89 |
| 6,090,101 A | 7/2000 | Quon et al. | 606/9 |
| 6,096,031 A | 8/2000 | Mitchell et al. | 606/15 |
| 6,130,900 A | 10/2000 | Black et al. | 372/25 |
| 6,139,712 A | 10/2000 | Patton et al. | 205/143 |
| 6,165,170 A | 12/2000 | Wynne et al. | 606/9 |
| 6,171,302 B1 | 1/2001 | Talpalriu et al. | 606/9 |
| 6,171,332 B1 | 1/2001 | Whitehurst | 607/89 |
| 6,190,376 B1 | 2/2001 | Asah et al. | 606/9 |
| 6,193,711 B1 | 2/2001 | Connors et al. | 606/12 |
| 6,235,016 B1 | 5/2001 | Stewart | 606/9 |
| 6,280,438 B1 | 8/2001 | Eckhouse et al. | 606/9 |
| 6,282,223 B1 | 8/2001 | Angeley | 372/92 |
| 6,289,236 B1 | 9/2001 | Koenig et al. | 600/477 |
| 6,379,376 B1 | 4/2002 | Lubart | 607/88 |
| 6,387,089 B1 | 5/2002 | Kreindel et al. | 606/9 |
| 6,451,010 B1 | 9/2002 | Angeley | 606/17 |
| 6,475,138 B1 | 11/2002 | Schechter et al. | 600/108 |
| 6,505,059 B1 | 1/2003 | Kollias et al. | 600/316 |
| 6,514,243 B1 | 2/2003 | Eckhouse et al. | 606/9 |
| 6,522,911 B1 | 2/2003 | Toida et al. | 600/473 |
| 6,544,585 B1 | 4/2003 | Hongo et al. | 216/18 |
| 6,702,838 B1 | 3/2004 | Andersen et al. | 607/89 |
| 6,766,187 B1 | 7/2004 | Black et al. | 600/473 |

FOREIGN PATENT DOCUMENTS

| | | |
|---|---|---|
| AU | 0691713 | 5/1998 |
| BE | 894290 | 3/1983 |
| CA | 1122156 | 4/1982 |
| CA | 1197563 | 12/1985 |
| CA | 1260116 | 9/1989 |
| CA | 2093055 | 10/1993 |
| CA | 2131750 | 1/1996 |
| CA | 2168624 | 8/1996 |
| CH | 416861 | 7/1966 |
| DE | 565331 | 11/1932 |
| DE | 2308554 | 8/1974 |
| DE | 2740179 | 3/1978 |
| DE | 2717421 | 11/1978 |
| DE | 27 17 421 A1 | 11/1978 |
| DE | 2740969 | 3/1979 |
| DE | 7901050 | 5/1979 |
| DE | 2901534 | 7/1979 |
| DE | 2846471 | 5/1980 |
| DE | 2948580 | 6/1980 |
| DE | 3220218 | 3/1983 |
| DE | 3330293 | 3/1985 |
| DE | 3804732 | 8/1989 |
| DE | 3906860 | 9/1989 |

| | | |
|---|---|---|
| DE | 4031320 A | 4/1992 |
| DE | 9304869 | 9/1993 |
| DE | 9321497 | 8/1998 |
| EP | 0003312 | 8/1979 |
| EP | 0052765 | 6/1982 |
| EP | 0075860 | 4/1983 |
| EP | 0172490 | 2/1986 |
| EP | 0185810 | 7/1986 |
| EP | 0198257 | 10/1986 |
| EP | 0240990 | 10/1987 |
| EP | 0310285 | 4/1989 |
| EP | 0324490 | 7/1989 |
| EP | 0335714 | 10/1989 |
| EP | 0429297 | 5/1991 |
| EP | 0480995 | 4/1992 |
| EP | 0527050 | 2/1993 |
| EP | 0565331 A2 | 10/1993 |
| EP | 0575274 | 12/1993 |
| EP | 0626229 | 11/1994 |
| EP | 0724292 | 7/1996 |
| EP | 0724894 | 8/1996 |
| EP | 0736308 | 10/1996 |
| EP | 0753285 A1 | 1/1997 |
| EP | 0763371 | 3/1997 |
| EP | 0807418 | 11/1997 |
| EP | 0880168 | 11/1998 |
| EP | 0885629 | 12/1998 |
| EP | 1078604 | 2/2001 |
| EP | 1078605 | 2/2001 |
| ES | 8306601 | 9/1983 |
| FI | 822940 | 3/1983 |
| FI | 0931608 | 10/1993 |
| FR | 2193628 | 2/1974 |
| FR | 2342745 | 9/1977 |
| FR | 2364038 | 4/1978 |
| FR | 2389229 | 11/1978 |
| FR | 2571264 | 4/1986 |
| GB | 1116465 | 6/1968 |
| GB | 2012939 | 8/1979 |
| GB | 2105195 | 3/1983 |
| GB | 2218660 | 11/1989 |
| HU | 181836 | 11/1983 |
| HU | 186081 | 5/1985 |
| IL | 101547 | 12/1996 |
| JP | 52109387 | 9/1977 |
| JP | 53105083 | 9/1978 |
| JP | 55117166 | 9/1980 |
| JP | 56109654 | 8/1981 |
| JP | 56124451 | 9/1981 |
| JP | 56137140 | 10/1981 |
| JP | 58086178 | 5/1983 |
| JP | 60006871 | 1/1985 |
| JP | 60132571 | 7/1985 |
| JP | 62114543 | 5/1987 |
| JP | 63277771 | 11/1988 |
| JP | 1034378 | 2/1989 |
| JP | 64012402 | 2/1989 |
| JP | 1240694 | 9/1989 |
| JP | 2154753 | 6/1990 |
| JP | 3016956 | 1/1991 |
| JP | H3-128069 | 5/1991 |
| JP | 3211287 | 9/1991 |
| JP | 3233986 | 10/1991 |
| JP | HEI-4-53569 | 2/1992 |
| JP | 4067860 | 3/1992 |
| JP | 4079966 | 3/1992 |
| JP | 4-90360 | 8/1992 |
| JP | 5001559 | 1/1993 |
| JP | 5029089 | 2/1993 |
| JP | 5111539 | 5/1993 |
| JP | 6063165 | 3/1994 |
| JP | 6198945 | 7/1994 |
| JP | 7008281 | 1/1995 |
| JP | 7275380 | 10/1995 |
| JP | 7308300 | 11/1995 |
| JP | 86266326 | 10/1996 |
| LU | 84349 | 6/1983 |
| SE | 416861 | 2/1981 |
| SE | 452852 | 12/1987 |
| SE | 465 953 B | 11/1991 |
| SE | 515325 | 7/2001 |
| SU | 1347142 | 10/1987 |
| WO | WO 80/02640 | 12/1980 |
| WO | WO 84/03049 | 8/1984 |
| WO | WO 84/04463 | 11/1984 |
| WO | WO 89/00871 | 2/1989 |
| WO | WO 89/11261 | 11/1989 |
| WO | WO 90/12545 | 11/1990 |
| WO | WO 90/14836 | 12/1990 |
| WO | WO 91/00063 | 1/1991 |
| WO | WO 91/12766 | 9/1991 |
| WO | WO 91/13652 | 9/1991 |
| WO | WO 91/15264 | 10/1991 |
| WO | WO 92/19165 | 11/1992 |
| WO | WO 93/08715 | 5/1993 |
| WO | WO 95/15725 | 6/1995 |
| WO | WO 96/21490 | 7/1996 |
| WO | WO 96/32895 | 10/1996 |
| WO | WO 96/33538 | 10/1996 |
| WO | WO 96/41577 | 12/1996 |
| WO | WO 97/37602 | 10/1997 |
| WO | WO 98/52645 | 11/1998 |
| WO | WO 99/25905 | 5/1999 |
| WO | WO 99/55243 | 11/1999 |
| WO | WO 00/32835 | 6/2000 |

OTHER PUBLICATIONS

Anderson et al., "Selective Photothermolysis: Precise Microsurgery by Selective Absorption of Pulsed Radiation", *Science*, 220:524–527 (Apr. 1993).

Anderson et al., "Pulsed photothermal radiometry in turbid media: internal reflection of backscattered radiation strongly influences optical dosimetry", *Applied Optics*, 28(12):2256–2262 (1989).

Anderson et al., "Microvasculature can be selectively damaged using dye lasers: basic theories and experimental evidence in human skin", *Laser in Surg. Med.*, 1:263–276 (1981).

Arthrex, Inc., "Single Use Shaver Blades and Burs", (1996).

Birngruber et al., "Fundus Reflectometry: A Step towards Optimization of the Retina Photocoagulation", *Mod. Probl. Ophthal.*, 18:383–390 (1977).

Blitzer, "Laser Photocoagulation in the Care of Patients with Osler—Weber—Rendu Disease", *Operative Techniques in Otolaryngology—Head and Neck Surgery*, 5(4):274–277 (Dec. 1994).

Boulnois, "Photophysical Processes in Recent Medical Laser Developments: A Review", *Lasers in Medical Science*, 1:47–64 (1986).

Brauner et al., "Treatment of Pigmented Lesions with the Flashlamp Pumped PL DL ("Brown Spot") Laser", *Laser Med. And Surgery Abstracts*, 4:73 (Sep. 1992).

Cisneros et al., "The Q–switched Neodymium (Nd): YAG Laser with Quadruple Frequency", *Dermatol. Surg.*, 24:345–350 (1998).

Dagan et al., "Microprocessor—Controlled Scanning Micromanipulator for Carbon—Dioxide Laser Surgery", *J. Neurosurgery*, 59:1098–1099 (Dec. 1983).

Fitzpatrick et al., "Treatment of Benign Cutaneous Pigmented Lesions with the Candela 510 NM Pulsed Laser", *Laser Med. and Surgery Abstracts,* 4S:73 (Sep. 1992).

Frauchiger et al., "Laser properties of selectively excited YA10.sub.3 :Er", *Optic Letters,* 13(11):964–966 (1988).

Gabay et al., "Modelling the Assessment of Port Wine Stain Parameters From Skin Surface Temperature Following a Diagnostic Laser Pulse", *Lasers in Surgery and Medicine,* 20(2):179–187 (1997).

Geeraets et al., "Light Reflectance of the Ocular Fundus", *Archives of Ophthalmology,* 69:612–617 (May 1963).

Gustafsson et al., "A Variable Pulsewidth Vascular System for Dermatology", *SPIE,* 2128:186–196 (1994).

Hacker et al., "The Effect of Flash Lamp–Pulsed Dye Laser on Psoriasis", *Archives of Dermatology,* 128:853–855 (Jun. 1992).

Hertoski et al., "Gaussian beam ray–equivalent modeling and optical design", *Applied Optics,* 22(8):1168–1174 (1983).

International Search Report, dated Jul. 24, 1996, for International Application No. PCT/US96/04515, 4 pages.

Ishimaru, "Diffusion of Light in Turbid Material", *Applied Optics,* 28(12):2210–2215 (1989).

Jacques et al., "The Role of Skin Optics in Diagnostic and Therapeutic Uses of Lasers", *Lasers in Dermatology,* 1–21 (1991).

Jerath et al., "Calibrated real–time control for lesion size based on reflectance images", *Applied Optics,* 32(7):1200–1209 (Mar. 1993).

Jerath et al., "Reflectance Feedback Control of Photocoagulation In Vivo", *Arch Ophthalmol,* 111:531–534 (Apr. 1993).

Jeys et al., "Sum fequency generation of sodium resonance radiation", *Applied Optics,* 28(13):2588–2591 (1989).

Kaufman et al., "Clinical Evaluation of Pulsed Erbium:YAG Laser Ablation in Cutaneous Surgery", (Abstract), *Partly Presented at 15th Annual Mtg of the American Society for LaserMedicine and Surgery,* (1995).

Kauvar et al., "Laser Therapy for Cutaneous Vascular Lesions", *Operative Techniques in Otolaryngology—Head and Neck Surgery,* 5(4):250–258 (Dec. 1994).

Kienle et al., "Why do veins appear blue? A new look at an old question", *Applied Optics,* 35(7):1151–1160 (1996).

Lahaye et al., "Optimal laser parameters for port wine stain therapy: a theoretical approach", *Phys. Med. Biol.* 30(6):573–587 (1985).

LaserSight Centers brochure, "CENTAURI.TM. Ophthalmic Erbium: Yag Laser", (Nov. 1993).

Lesinski et al., "Carbon Dioxide Lasers for Otosclerosis", *Otolaryngologic Clinics of North America,* 26(3)417–441 (Jun. 1993).

Lewis et al., "Backscattering target detection in a turbid medium by polarization discrimination", *Applied Optics,* 38(18):3937–3944 (Jun. 1999).

Lytle et al., "Improved Efficacy of SnET2 Mediated PDT With the Simultaneous Application of Selective Laser–Indused Hyperthermia", *SPIE Proceedings,* 2392–6:15–22.

Maloney et al., "Laser Otology", *Operative Techniques in Otolaryngology—Head and Neck Surgery,* 3(2):74–83 (Jun. 1992).

Milner et al., "Depth determination of chromophores in human skin by pulsed photothermal radiometry," *Applied Optics,* 35(19):3379–3385 (Jul. 1996).

Milner et al., "Depth profiling of laser–heated chromophores in biological tissues by pulsed photothermal radiometry," *Journal of the Optical Society of America A,* 12(7):1479–1488 (Jul. 1995).

Minamihaba et al., "Double–Level CU Inlaid Interconnects with Simultaneously Filled Viaplugs" *Japanese Journal of Applied Physics,* 35(2B):1107–1110 (Feb. 1996).

Mordon et al., "Relation Between Skin Surface Temperature and Minimal Blanching During Argon, Nd–YAG 532, and CW Dye 585 Laser Therapy of Port–Wine Stains," *Lasers in Surgery and Medicine,* 13(1):124–126 (1993).

Morreli et al., "Tunable Dye Lasers (577 nm) Treatment of Port Wine Stains", *Lasers Surg. Med.,* 6(1):94–99 (1986).

Orenberg et al., "Comparison of heat delivery systems for hyperthermia treatment of psoriasis", *Int. J. Hyperthermia,* 2(3):231–241 (1986).

Pai et al., "Selective Electroless Copper for FLSI Interconnection", *IEEE Electron Device Letters,* 10(9):423–425 (1989).

Patent Abstracts of Japan, vol. 012, No. 337 (E–657), Sep. 12, 1988 & JP 63 100749 A (Hitachi Ltd.), May 2, 1988.

Patents Abstracts of Japan, vol. 016, No. 263 (D–1216), Jun. 15, 1992 & JP 04 051125 A (Kanegafuchi Chem. Ind. Co. Ltd.), Feb. 27, 1992.

Patent Abstracts of Japan, vol. 018, No. 480 (E–1603), Sep. 8, 1994 & JP 06 164140 A (Ibiden Co. Ltd.), Jun. 10, 1994.

Patent Abstracts of Japan, vol. 4, No. 172 (P–038), Sep. 9, 1980.

Petrovich et al., "Relationship of Response to Transurethral Hyperthermia and Prostate Volume in BPH Patients", *Urology,* 40(4):317–321 (Oct. 1992).

Polla, et al., "Tunable Pulsed Dye Laser for the Treatment of Benign Cutaneous Vascular Ectasia", *Drematologica,* 174:11–17 (1987).

Pomerantzeff et al., "A Method to Predetermine the Correct Photocoagulation Dosage", *Arch Ophthalmol,* 101:949–953 (1983).

Pomerantzeff et al., "Time and Location Analysis of Lesion Formation in Photocoagulation", *Arch Ophthalmol,* 101:954–957 (1983).

Sausville et al., "Blue Lamps in Phototherapy of Hyperbilrubinemia", *Journal of IES,* 112–118 (1972).

Semm et al., "Tissue Morcellation In Endoscopic Surgery", *Surgical Technology International V, International Developments in Surgery & Surgical Research,* 175–178. (1996).

Slatkin et al., "Instrumentation for Office Laser Surgery", *Operative Techniques in Otolaryngology—Head and Neck Surgery,* 5(4):211–217 (Dec. 1994).

Smith & Nephew, Inc., "Shaver Systems–Endoscopic Powered Instrument System", Mar. 1997.

Smith et al., "The Design of Optical Systems", *Modern Optical Engineering,* 273–278 (1990).

Smithies et al., "The Effect of the Illumination Time When Treating Port–wine Stains", *Lasers in Medical Science,* 10(2):93–104 (1995).

Taylor et al., "Light & Electron Microscopic Analysis of Tattoos Treated by O–Switched Ruby Laser", *J. of Investigative Dermatology,* 97:131–136 (1991).

Van–Gemert et al. "Treatment of Port–Wine Stains: Analysis", *Medical Instrumentation,* 21:213–217 (1987).

Waldow et al., "Nd:YAG Laser–Induced Hyperthermia in A Mouse Tumor Model", *Lasers in Surgery and Medicine,* 8(5)510–514 (1988).

Weinberg et al., "The Change in Light Reflection of the Retina During Therapeutic Laser–Photocoagulation," *IEEE J. Quantum Electronics,* QE–20(12):1481–1489 (1984).

Wright et al., "Initial in vivo results of hybrid retinal photocoagulation system", *Journal of Biomedical Optics,* 5(1):56–61 (Jan. 2000).

Yang et al., "Automatic Control of Lesion Size in a Simulated Model of the Eye", *IEEE Journal of Quantum Electronics,* 26(12):2232–2239 (1990).

Yang et al., "Reflectance as an Indirect Measurement of the Extent of Laser–Induced Coagulation," *IEEE Transactions on Biomedical Engineering,* 37(5):466–473 (1990).

Zee et al., "Whole–Body Hyperthermia in Cancer Therapy: A Report of A Phase I–II Study" *Eur. J., Cancer Clinical Oncology,* 19(9):1189–1200 (1983).

Zimmer information brochure, "Arthroscopic Blades and Burrs", (1996).

File history for EP0565331, Various Dates.

Deposition transcript of Lars Ake Morgan Gustavsson (Dec. 10, 2007).

*Lumenis Ltd., et al. v. Alma Ltd., et al.,* 07:CV3622, N.D.III.—Complaint (Jun. 28, 2007).

*Lumenis Ltd., et al. v. Alma Ltd., et al.,* 07:CV3622, N.D.III.—Joint Claim Construction Statement (Jan. 4, 2008).

*Lumenis Ltd., et al. v. Alma Ltd., et al.,* 07:CV3622, N.D.III.—Plaintiffs' Opening Claim Construction Brief) (Jan. 7, 2008).

*Lumenis Ltd., et al. v. Alma Ltd., et al.,* 07:CV3622, N.D.III.—Plaintiffs' Reply to Defendants' Responsive Claim Construction Brief (Jan. 22, 2008).

*Lumenis Ltd., et al. v. Alma Ltd., et al.,* 07:CV3622, N.D.III.—Plaintiffs' Demonstratives for Markman Hearing (Jan. 23, 2008).

*Lumenis Ltd., et al. v. Alma Ltd., et al.,* 07:CV3622, N.D.III.—Defendants' Amended Answer, Affirmative Defenses, and Counterclaims (Jan. 25, 2008).

*Lumenis Ltd., et al. v. Alma Ltd., et al.,* 07:CV3622, N.D.III.—Plaintiffs' Reply to Defendants' Counterclaim (Feb. 14, 2008).

*Lumenis Ltd., et al. v. Alma Ltd., et al.,* 07:CV3622, N.D.III.—Plaintiffs' Further Supplemental Answers to Defendants' First Set of Interrogatories to Plaintiffs (Nos. 3 and 11) (Feb. 1, 2008).

*Lumenis Ltd., et al. v. Alma Ltd., et al.,* 07:CV3622, N.D.III.—Plaintiffs' Rule 26(a)(1) Initial Disclosures to Defendants (Oct. 29, 2007).

*Lumenis Ltd., et al. v. Alma Ltd., et al.,* 07:CV3622, N.D.III.—Defendants' Initial Disclosures Pursuant to Fed. R. Civ. P. 26(a) (Oct. 29, 2007).

*Lumenis Ltd., et al. v. Alma Ltd., et al.,* 07:CV3622, N.D.III.—Plaintiffs' Answers to Defendants' First Set of Interrogatories to Plaintiffs (Nov. 19, 2007).

*Lumenis Ltd., et al. v. Alma Ltd., et al.,* 07:CV3622, N.D.III.—Plaintiffs' Supplemental Answers to Defendants' First Set of Interrogatories to Plaintiffs (Nos. 2, 5, 8 & 15) (Dec. 14, 2007).

*Lumenis Ltd., et al. v. Alma Ltd., et al.,* 07:CV3622, N.D.III.—Plaintiffs' Further Supplemental Answers to Defendants' First Set of Interrogatories to Plaintiffs (Nos. 7, 11, and 12) (Dec. 21, 2007).

*Lumenis Ltd., et al. v. Alma Ltd., et al.,* 07:CV3622, N.D.III.—Plaintiffs' Further Supplemental Answers to Defendants' First Set of Interrogatories to Plaintiffs (No. 3) (Dec. 27, 2007).

*Lumenis Ltd., et al. v. Alma Ltd., et al.,* 07:CV3622, N.D.III.—Plaintiffs' Answers to Defendants' Second Set of Interrogatories to Plaintiffs (Nos. 16–18) (Dec. 28, 2007).

*Lumenis Ltd., et al. v. Alma Ltd., et al.,* 07:CV3622, N.D.III.—Plaintiffs' Supplemental Answers to Defendants' Second Set of Interrogatories to Plaintiffs (No. 18) (Jan. 14, 2008).

Groot & Johnson, "Lasers and Advanced Dermatological Instrumentation", *Australas J. Dermatol.,* 28:77–85 (1987).

Kaufmann et al., "Pulsed Er: Yag—and Anm 308 UV–Excimer Laser: An In Vitro and In Vivo Study of Skin–Ablative Effects", Laser Surg. Med., 9:132–140 (1989).

Gros, et al, Diaphanologie Mammaire, Memoires Originaux, *J. Radiol. Electrol.,* 53(4):297–306 (1972), in French, with English translation.

Brochure for an Infrared Coagulator by Redfield Corporation (1968).

Goldman, *Biomedical Aspects of the Laser—An Introduction of Laser Applications into Biology and Medicine,* chapters 1, 2, 23 and index (1967).

Gossman et al., "Experimental Comparison of Laser and Cryosurgical Cilia Destruction", *Ophthalmic Surgery,* 23(3):179–182 (Mar. 1992).

Gossman et al., "Prospective Evaluation of the Argon Laser in the Treatment of Trichiasis", *Ophthalmic Surgery,* 23(3):183–187 (Mar. 1992).

"The Spectrum RD–1200 Q–Switched Ruby Laser", (Not Dated).

ESC Medical Systems, "Control of Pulse Duration and Pulse Secuence Delays for Effective Photo–Epilation", *EpiLight Hair Removal System Application Notes,* 3(2) (1997).

Geronemus, "Laser and Pulsed Light Source Treatment of Leg Vessels", (Sep. 1995).

Goldman, "Effects of New Laser Systems on the Skin", *Arch Dermatol,* 108(3):385–90 (Sep. 1973).

Goldman, "Treating Varicose and Telangiectatic Leg Veins", *Federal Practitioner* (Mar. 1997).

Kincade, "New Procedures push tissue studies beneath the surface", *Laser Focus World,* pp. 57–63, (Aug. 1995).

"Aesthetic CO2 Laser System", literature, 2 pages, (Aug. 1994).

"New Laser for Microlaryngeal Surgery", *I.L.. Med. Newsletter,* 1(1) (Spring 1991).

"The Er:YAG Laser System for ophthalmic microsurgery", *Aesculap Meditec brochure,* 2 pages, (Oct. 1994).

"The Proven Solution for Disk, Spinal Cord and Brain Microsurgery", *I. L. Med. Unilase product info. Brochure* (1993).

"The Proven Solution for Otologic and Microlaryngeal Surgery", *I. L. Med. Unilase product info. Brochure* (1993).

"Using a CO2 Laser During Conventional Microdiskectomy Shows Promise of Faster Recovery", *I.L. Med Newsletter,* 1(4) (Spring 1991).

"Control of Pulse Duration and Pulse Sequence Delays for Effective Photo–Epilation", *EpiLight™ Application Notes,* 3(2) (1997).

Adrian, "LightSheer™ 800 NM Pulsed, High–Power Diode Laser Hair Removal System", (2002).

Adrian, "Tissue Effects of a New Long Pulse Frequency Doubled 532 nm Neodymium: YAG Laser on Vascular Lesions", (2001).

Adrian, "Treatment of Facial Telangiectasia Using the VersaPulse® Variable Pulse Width Frequency Doubled Neodymium:YAG Laser: A Case Report", (2001).

Anderson et al., "Microvasculature Can Be Selectively Damaged Using Dye Lasers: A Basic Theory and Experimental Evidence in Human Skin", *Laser in Surgery and Medicine,* 1:263–276 (1981).

Anderson et al., "The Optics of Human Skin", *The Journal of Investigative Dermatology,* 77(1):13–19 (Jul. 1981).

Anderson et al., "Laser Hair Removal—A Lecture Presented to the 77th Congress of the Japan Society of Aesthetic Surgery", (Nov. 1999).

Bandel, "Effective Resolution of a Mature Port–Wine Stain Using PhotoDerm®VL", *Clinical Application Notes,* 1(2) (1998).

Bartley et al., "An Experimental Study to Compare Methods of Eyelash Ablation", *Ophthalmology,* 94(10):1286–1289 (Oct. 1987).

Battle et al., "Study of Very Long–Pulsed (100 ms) High–Powered Diode Laser for Hair Reduction on All Skin Types", (2002).

Beasley et al., "New Parameters for Intense Pulsed Light Rejuvenation With a Thermoelectrically Chilled Crystal Delivery System", *Cosmetic Dermatology,* 15(7):14–16 (Jul. 2002).

Bitter, "Noninvasive Rejuvenation of Photodamaged Skin Using Serial, Full–Face Intense Pulsed Light Treatments", *Dermatol Surg.* , 26(9):835–43 (Sep. 2000).

Campos et al., "Use of an 800 nm High–power Diode Laser for the Treatment of Leg Vein Telangiectasia", (2002).

Campos, "Safe and Effective Long–Term Hair Reduction in Tanned Patients Using an 800 nm Diode Laser", (2002).

Del Giglio, "Hair Removal Using a Combination of Electrical and Optical Energies—3–Month Clinical Study", 1–4 (Not Dated).

Del Giglio, "Hair Removal Using a combination of Electrical and Optical Energies: Multiple Treatments Clinical Study—Six–Month Follow up", 1–4 (Not Dated).

Dierickx et al., "Effective, Permanent Hair Reduction Using a Pulsed, High–Power Diode Laser", (2002).

Dierickx, "Laser Hair Removal: Scientific Principles and Pratical Aspects", (2002).

Dover et al., "Pigmented Guinea Pig Skin Irradiated With Q–Switched Ruby Laser Pulses", *Arch Dermatol,* 125(1):43–44 (Jan. 1989).

Dréno et al., "The Benefit of Chilling in Argon–Laser Treatment of Port–Wine Stains", *Plast Reconstr Surg.,* 75(1):42–45 (Jan. 1985).

Dzubow, "Leg Veins and Stretch Marks—Have They Seen the Light?", *Dermatol Surg.,* 22(4):321 (Apr. 1996).

Eckhouse et al., "The Application of Selective Photothermolysis in Treating Leg Veins and Other Benign Vascular Lesions", (Apr. 1996).

ESC Medical Systems, "Eliminating Multicolored Tattoos with PhotoDerm® PL", *PhotoDerm® PL Application Notes,* 2(2) (1997).

ESC Medical Systems, "Facial and truncal angionas—treating patients quickly and effectively", *PhotoDerm® Application Notes,* 1(2) (1996).

ESC Medical Systems, "How does it look in theory?", (1996).

ESC Medical Systems, "Significance of Wavelength Range for Effective Hair Photo–Epilation", *EpiLight Hair Removal System Application Notes,* 3(1) (1997).

ESC Medical Systems, "Superior Treatment of Benign Pigmented Lesions with PhotoDerm® PL", *PhotoDerm® PL Application Notes,* 2(1) (1997).

ESC Medical Systems, "Why are leg veins so difficult to treat?", *PhotoDerm®VL Application Notes,* 1(1) (1996).

Gilchrest et al., "Chilling Port Wine Stains Improves the Response to Argon Laser Therapy", *Plast Reconstr Surg.,* 69(2):278–83 (Feb. 1982).

Gold et al., "Intense Pulsed Light (IPL™) System Enables Successful Treatment of Skin Type VI", *Clinical Application Notes,* 2(5) (2000).

Gold et al., "Long–term epilation using the EpiLight broad band, intense pulsed light hair remvoval system", *Dermatol Surg.,* 23(10):909–913 (Oct. 1997).

Gold, "Treatment of Larger and Deeper Varicosities Utilizing a 1064 nm Laser System", *Cosmetic Dermatology,* (Nov. 2000).

Goldman, "Effects of New Laser Systems on the Skin" *Arch. Dermatol.,* 108:385–390 (Sep. 1973).

Goldman et al., "Impact of the Laser on Nevi and Melanomas", *Arch Dermatol,* 90:71–75 (Jul. 1964).

Goldman et al., "Laser Treatment of Tattoos—A Preliminary Survey of Three Year's Clinical Experience", *JAMA,* 201(11):163–166 (Sep. 1967).

Goldman et al., "Long–Term Laser Exposure of a Senile Freckle", *Arch. Environ. Health,* 22:401–403 (Mar. 1971).

Goldman et al., "Pathology of the Effect of the Laser Beam on the Skin", *Nature,* 197:912–914 (Mar. 1963).

Goldman et al., "Photothermal Sclerosis of Leg Veins", *Dermatol Surg.,* 22(4):323–30 (Apr. 1996).

Goldman et al., "Preliminary Investigation of Fat Embolization from Pulsed Ruby Laser Impacts of Bone", *Nature,* 221:361–363 (Jan. 1969).

Goldman et al., "Radiation from a Q–Switched Ruby Laser, Effect of Repeated Impacts of Power Output of 10 Megawatts on a Tatto of Man", *The Journal of Investigative Dermatology,* 44:69–71 (Jan. 1965).

Goldman et al., "Replica Microscopy and Scanning Electron Microscopy of Laser Impacts on the Skin", *The Journal of Investigative Dermatology,* 52(1):18–24 (Jan. 1969).

Goldman et al., "The Biomedical Aspects of Lasers", *JAMA,* 188(3):230–234 (Apr. 1964).

Goldman et al., "The Effect of Repeated Exposures to Laser Beams", *Acta derm.–venereol,* 44:264–268 (1964).

Goldman et al., "Treating Varicose and Telangiectatic Leg Veins", *Federal Practitioner,* (Mar. 1997).

Goldman et al., "Treatment of Basal Cell Epithelioma by Laser Radiation", *JAMA,* 189:773–5 (Sep. 1964).

Goldman, "Dermatologic manifestations of laser radiation", S92–S93 (Not Dated).

Goldman, "Laser Surgery for Skin Cancer", *New York State Journal of Medicine,* (Oct. 1977).

Goldman, "One Laser For A Cosmetic Dermatologic Practice", *Cosmetic Dermatology,* 15(7):49–50 (Jul. 2002).

Goldman, "Surgery by Laser for Malignant Melanoma", *J. Dermatol. Surg. Oncol.,* 5(2) (Feb. 1979).

Goldman, "The Skin", *Arch Environ Health,* 18:434–436 (Mar. 1969).

Herloski et al., "Gaussian beam ray–equivalent modeling and optical design", *Applied Optics,* 22(8):1168–1174 (Apr. 1983).

Huang et al., "Intense Pulsed Light for the Treatment of Facial Freckles in Asian Skin", *Dermatol Surg.,* 29(11):1008–1012 (Nov. 2002).

Hunt et al., "Treatment of Large Body Areas with EpiLight® Hair Removal System: Multi–Center Back Epilation", *Clinical Application Notes,* 2(2):1–4 (1998).

Inderfurth et al., "Dynamic Reflectometer for Control of Laser Photocoagulation on the Retina", *Lasers in Surgery and Medicine,* 15(1):54–61 (May 1994).

Jay, "Photo–Epilation with the EpiLight™ Hair Removal System: Multi–case Study", *Clinical Application Notes,* 2(3) (1998).

Johnson et al., "Intense pulsed light treatment of hirsutism: case reports of skin phototypes V and VI", *Journal of Cutaneous Laser Therapy,* 1:233–237 (1999).

Karpen, "Treating Benign Vascular Lesions of the Lower Extremities: Past, Present, and Future", *Journal of Clinical Laser Medicine & Surgery,* 12(2):111–112 (1994).

Kautz et al., "Early Intervention in Pediatric Hemagiomas with the VascuLight™ Intense Pulsed Light / Laser Source", *Clinical Application Notes,* 8(4) (2000).

Kazmi, "Laser Hair Removal with an 800nm Diode Laser–A Retrospective Study of 1000 Women with Skin Types II to VI", (Jun. 2002).

Klavuhn, "Coverage Rate: The Influence of Laser Parameters on Treatment Time", *Laser Hair Removal Note No. 3,* (Mar. 2000).

Klavuhn, "Epidermal Protection: A Comparative Analysis of Sapphire Contact and Cryogen Spray Cooling", *Laser Hair Removal Technical Note No. 1,* (Jan. 2000).

Klavuhn, "Illumination Geometry: The Importance of Laser Beam Spatial Characteristics", *Laser Hair Removal Technical Note No. 2,* (Feb. 2000).

Kono et al., "Diode Laser–Assisted Hair Removal in Asians: A Study of 101 Japanese Patients", (2000).

Kreindel et al., "Electro–Optical Synergy (ELOS™) Technology for Aesthetic Medicine—Light Triggering Effect on RF Selectivity", 1–4, (Not Dated).

Kreindel et al., "Electro–Optical Synergy (ELOS™) Technology for Aesthetic Medicine Advantages and limitations of various forms of electromagnetic energy for safe and effective hair removal", 1–4 (Not Dated).

Kuriloff et al., "Pharyngoesophageal hair growth: The role of laser epilation", *Otolaryngol Head Neck Surg.,* 98(4):342–5 (Apr. 1988).

Lask et al., "The role of laser and intense light sources in photo–epilation: a comparative evaluation", *Journal of Cutaneous Laser Therapy,* 1:3–13 (1999).

Laughlin, "Effective Epilation of a white hair using combined radio–frequency and otpical energy", (Not Dated).

Laughlin, "Epilation in dark skin (types V and VI) with integrated radio–frequency and optical energy", 23–26 (Not Dated).

Levy, "Intense pulsed light treatment for chronic facial erythema of systemic lupus erythematosus: a case report", *Journal of Cutaneous Laser Therapy,* 2(4):195–198 (Dec. 2000).

Lou et al., "Prospective Study of Hair Reduction by Diode Laser (800nm) with Long–Term Follow–Up", *Dermatol Surg.,* 26(5):428–432 (May 2000).

Lumenis Inc., "IPL Skin Treatments using Photorejuvenation: helps restore the skin's youthful look", (2002).

Lumenis Inc., "VascuLight: Intense Pulsed Light and Laser Technology", (2002).

Lumenis Inc., "VascuLight Elite: Intense Pulsed Light and Laser Technology", (2002).

McCoy et al., "An Evaluation of the Copper–Bromide Laser for Treating Telangiectasia", *Dermatol. Surg.,* 22:551–557 (1996).

Moraga, "European Multi–Center Study: VascuLight® for the Treatment of Varicose Veins and Leg Telangiectasias, as well as Other Vascular Lesions", *Clinical Application Notes,* 8(1) (2001).

Moretti, "IPL Photorejuvenation Popularity Spreads Rapidly", *Aesthetic Buyers Guide,* (Mar. 2001).

Moretti, "Laser–Based Technology Expands Treatment Options", *Medical Laser Insight,* (Apr. 1997).

Negishi et al., "Full–Face Photorejuvenation of Photodamged Skin by Intense Pulsed Light with Integrated Contact Cooling: Initial Experiences in Asian Patients", *Lasers in Surgery and Medicine,* 30(4): 298–305 (2002).

Negishi et al., "Photorejuvenation for Asian Skin by Intense Pulsed Light", *Dermatol Surg.,* 27:7:627–32 (Jul. 2001).

Nestor et al., "Photorejuvenation Non–Ablative Skin Rejuvenation Using Intense Pulse Light" (Not dated).

Pardo et al., "Use of the LightSheer™ Diode Laser System for Hair Reduction: Safety and Efficacy in a Large Series of Treatments", (Feb. 2001).

Parrish et al., "Selective Thermal Effects with Pulsed Irradiation from Lasers: From Organ to Organelle", *The Journal of Investigative Dermatology,* 80(6):75s–80s (Jun. 1963).

Pervaiz et al., "A New Method of Quatitating Damage to the Hair Shaft: Its Application to Ultraviolet–and Radio Frequency–Treated Hair", *Annals New York Academy of Sciences,* 642:491–2 (Dec. 1991).

Polla et al., "Melanosomes Are a Primary Target of Q–Switched Ruby Laser Irradiation in Guinae Pig Skin", *The Journal of Investigative Dermatology,* 89(3):281–6 (Sep. 1987).

Raulin et al, "Treatment of a Nonresponding Port–Wine Stain With a New Pulsed Light Source (PhotoDerm®VL)", *Lasers Surg Med.,* 21(2):203–8 (1997).

Raulin et al., "Effective Treatment of Hypertrichosis with Pulsed Light: A Report of Two Cases", *Annals of Plastic Surgery,* 39(2):169–173 (Aug. 1997).

Raulin et al., "Photoderm VL®—efficiency and limitations of an Intense pulsed light source", *Australasian Journal of Dermatology,* 38(2) (Jun. 1997) (Abstract Only).

Raulin et al., "Treatment of of Adult Port–Wine Stains Using Intense Pulsed Light Therapy (PhotoDerm®VL): Brief Initial Clinical Report", *Dermatol Surg,* 23(7):594–7 (Jul. 1997).

Raulin et al., "Treatment of benign venous malformation with an intense pulsed source (PhotoDerm®VL)", Europena Journal of Dermatology 7(4):279–285 (Jun. 1997).

Riggle et al., "Laser Effects on Normal and Tumor Tissue", 35–63 (Not Dated).

Sadick et al., "Advances in Laser Surgery for Leg Veins: Bimodal Wavelength Approach to Lower Extremity Vessels, New Cooling Techniques, and Longer Pulse Durations", *Dermatol Surg.,* 28:1:16–20 (Jan. 2002).

Sadick et al., "Long–term Photoepilation Using a Broad–spectrum Intense Pulsed Light Source", *Arch Dermatol,* 136:1336–1340 (Nov. 2000).

Sadick, "A dual wavelength approach for laser/intense pulsed light source treatment of lower extremity veins", *J Am Acad Dermatol,* 46(1):66–72 (Jan. 2002).

Sadick, "The Role of Combined Intense Pulsed Light/Radiofrequency Technology in the Management of Blond and White Hair Photoepilation", (Feb. 8, 2003, ISHR, Aspen, Colorado).

Schroeter et al., "An Intense Light Source", *Dermatol. Surg.,* 24:743–748 (1998).

Schroeter et al., "Clinical significance of an intense, pulsed light source on leg telangiectasias of up to 1 mm diameter", *Eur J Dermatol,* 7:38–42 (Jan.–Feb. 1997).

Shimbashi et al., "Ruby Laser Treatment of Pigmented Skin Lesions", *Aesth. Plast. Surg.,* 19(3):225–9 (1995).

Svaasand et al., "On the physical rationale of laser induced hyperthermia", 65–81 (Not Dated).

Taylor et al., "Treatment of Tattoos by Q–Switched Ruby Laser", *Arch Dermatol,* 126(7): 893–9 (Jul. 1990).

Troxler, "One Clinic's Experience in the Treatment of Varicose Veins and Leg Telangieactasias with the VascuLight™ Intense Pulsed Light / Nd:YAG Laser Source", *Clinical Applications Notes,* 8(3) (2001).

Waldman et al., "Cutaneous inflammation: Effects of hydroxy acids and eicosand inhibitors on vascular permeability", *The Journal of Investigative Dermatology,* 88:523 (1987) (Abstract Only).

Warren, "Pigmentation induction by melanocyte stimulating hormone in human skin culture", *The Journal of Investigative Dermatology,* 88:523 (1987) (Abstract Only).

Wastek et al., "Characterization of H–substance P (SP) binding to a mouse monoclonal mast cell line", *The Journal of Investigative Dermatology,* 88:523 (Abstract Only).

Watanabe et al., "The effect of pulse duration on selective pigmented cell injury by dye lasers", *The Journal of Investigative Dermatology,* 88:523 (1987) (Abstract Only).

Weir et al., "Photo–assisted epilation—review and personal observations", *Journal of Cutaneous Laser Therapy,* 1:135–143 (1999).

Weis et al., "Intense pulsed light: newer perspective", *Dermatol. Surg.,* 23(10):941–945 (1997).

Weiss et al., "New Treatment for Telangiecases and Venulectases: Status of Intense Pulsed Light Therapy", (Not Dated).

Weiss et al., "Sclerotherapy in the U.S.", *Dermatol. Surg.,* 21:393–396 (1995).

Weissman et al., "Growth, collogen and glycosaminoglycan synthesis by dermal firbroblasts derived from puva treated and psoriatic patients", *The Journal of Investigative Dermatology,* 88:523 (1987) (Abstract Only).

Welsh et al., "Evaluation of Cooling Techniques for the Protection of the Epidermis During ND–YAG Laser Irradiation of the Skin", *Neodymium–YAG Laser in Medicine and Surgery,* (1983).

Werner et al., "New possibilities of epilation with a high energy flash lamp", (Not Dated).

Wertz et al., "Effects of essential fatty acid deficiency on the structure and function of epidermal lipids", *The Journal of Investigative Dermatology,* 88:523 (1987) (Abstract Only).

Wheeland, "Laser–Assisted Hair Removal", *Dermatol Clin.,* 15(3):469–477 (Jul. 1997).

Woo, "Using EpiLight® for Hair Removal Treatment of Fitzpatrick Skin Types IV and V", *Clinical Application Notes,* 2(3):1–4 (1998).

Yanai et al., "Argon Laser Therapy of Port–Wine Stains: Effects and Limitations", *Plastic and Reconstructive Surgery,* 75(4):520–525 (Apr. 1985).

Yules et al., "The Effect of Q–Switched Ruby Laser Radiation on Dermal Tattoo Pigment in Man", *Arch Surg,* 95 (Aug. 1967).

Zeitler et al., "Laser Characteristics that Might be Useful in Biology", Chapter 1, 1–18 (Not Dated).

Zelickson et al., "EpiLight® Treatment of Hair Removal Using the Circulating Cutaneous Cooling Device: Preliminary Study Report" (Not Dated).

Goldman et al., "Effect of the Laser Beam on the Skin", *The Journal of Investigative Dermotology,* 40:121–122 (Mar. 1963).

Westinghouse Engineer, "Special Blue Lamp Helps Treat Jaundice in Newborn Infants", 31(1) (Jan. 1971).

*Lumenis Ltd., et al. v. Syneron Medical Ltd., et al.,* 2:02–cv–08269–ABC–PLA, C.D. CA.—Syneron Inc.'s Answer to Plaintiffs' Complaint (Nov. 19, 2002).

*Lumenis Ltd., et al. v. Syneron Medical Ltd., et al.,* 2:02–cv–08269–ABC–PLA, C.D. CA.—Syneron Medical Ltd.'s Answer to Plaintiffs' Complaint (Dec. 9, 2002).

*Lumenis Ltd., et al. v. Syneron Medical Ltd., et al.,* 2:02–cv–08269–ABC–PLA, C.D. CA.—Appendix of Dictionary References in Support of Plaintiffs' Report to Court–Appointed Expert (Jan. 9, 2003).

*Lumenis Ltd., et al. v. Syneron Medical Ltd., et al.,* 2:02–cv–08269–ABC–PLA, C.D. CA.—Syneron's Appendix of Prior Art References Discussed in Declaration of Dr. Warren S. Grundfest (May 8, 2003).

*Lumenis Ltd., et al. v. Syneron Medical Ltd., et al.,* 2:02–cv–08269–ABC–PLA, C.D. CA.—Plaintiff's Report to Court–Appointed Expert Dr. Bahram (Dec. 30, 2002).

*Lumenis Ltd., et al. v. Syneron Medical Ltd., et al.,* 2:02–cv–08269–ABC–PLA, C.D. CA.—Complaint for Patent Infringement (Oct. 30, 2002).

*Lumenis Ltd., et al. v. Syneron Medical Ltd., et al.,* 2:02–cv–08269–ABC–PLA, C.D. CA.—Declaration of Alon Maor in Support of Plaintiffs' Motion for Preliminary Injunction (Apr. 25, 2003).

*Lumenis Ltd., et al. v. Syneron Medical Ltd., et al.,* 2:02–cv–08269–ABC–PLA, C.D. CA.—Declaration of Alon Maor in Support of Plaintiffs' Ex Parte Application for Temporary Retraining Order and Order to Show Cause Re Preliminary Injunction (Oct. 30, 2002).

*Lumenis Ltd., et al. v. Syneron Medical Ltd., et al.,* 2:02–cv–08269–ABC–PLA, C.D. CA.—Declaration of Benjamin J. Fox in Opposition to Plaintiffs' Motion for a Preliminary Injunction (May 8, 2003).

*Lumenis Ltd., et al. v. Syneron Medical Ltd., et al.,* 2:02–cv–08269–ABC–PLA, C.D. CA.—Declaration of Domenic Serafino Re: Plaintiffs' Motion for Preliminary Injunction and Posting of Bond (Jul. 25, 2003).

*Lumenis Ltd., et al. v. Syneron Medical Ltd., et al.,* 2:02–cv–08269–ABC–PLA, C.D. CA.—Declaration of Dr. Michael Kreindel in Opposition to Motion for Preliminary Injunction (May 8, 2003).

*Lumenis Ltd., et al. v. Syneron Medical Ltd., et al.,* 2:02–cv–08269–ABC–PLA, C.D. CA.—Declaration of Dr. Warren S. Grundfest in Support of Syneron's Opposition to Plaintiffs' Motion for Preliminary Injunction (May 8, 2003).

*Lumenis Ltd., et al. v. Syneron Medical Ltd., et al.,* 2:02–cv–08269–ABC–PLA, C.D. CA.—Declaration of Felix T. Woo in Support of Plaintoffs' Motion for Preliminary Injunction (May 20, 2003).

*Lumenis Ltd., et al. v. Syneron Medical Ltd., et al.,* 2:02–cv–08269–ABC–PLA, C.D. CA.—Declaration of Felix T. Woo in Support of Plaintiffs' Ex Parte Application for Temporary Restraining Order and order to Show Cause Re Preliminary Injunction (Oct. 30, 2002).

*Lumenis Ltd., et al. v. Syneron Medical Ltd., et al.,* 2:02–cv–08269–ABC–PLA, C.D. CA.—Declaration of Harry F. Manbeck, Jr. in Response to Expert Report of Gerald J. Mossinghoff (May 27, 2003).

*Lumenis Ltd., et al. v. Syneron Medical Ltd., et al.,* 2:02–cv–08269–ABC–PLA, C.D. CA.—Declaration of John M. May in Support of Opposition to Plaintiffs' Ex Parte Application for Temporary Restraining Order and Order to Show Cause Regarding Preliminary Injunction (Nov. 1, 2002).

*Lumenis Ltd., et al. v. Syneron Medical Ltd., et al.,* 2:02–cv–08269–ABC–PLA, C.D. CA.—Declaration of Jordan A. Sigale in Support of Lumenis' Response to Syneron's Objections to Lumenis' Proposed Order Re: Preliminary Injunction and Posting of Bond (Jul. 31, 2003).

*Lumenis Ltd., et al. v. Syneron Medical Ltd., et al.,* 2:02–cv–08269–ABC–PLA, C.D. CA.—Declaration of Laura A. Wytsma in Support of Plaintiffs' Ex Parte Application for Temporary Restraining Order and Order to Show Cause Re Preliminary Injunction (Oct. 30, 2002).

*Lumenis Ltd., et al. v. Syneron Medical Ltd., et al.,* 2:02–cv–08269–ABC–PLA, C.D. CA.—Declaration of Moshe Mizrahy in Opposition to Plaintiffs' Motion for a Preliminary Injunction (May 8, 2003).

*Lumenis Ltd., et al. v. Syneron Medical Ltd., et al.,* 2:02–cv–08269–ABC–PLA, C.D. CA.—Declaration of Moshe Mizrahy in Support of Opposition to Plaintiffs' Ex Parte Application for Temporary Restraining Order and Order to Show Cause Re Preliminary Injunction (Nov. 1, 2002).

*Lumenis Ltd., et al. v. Syneron Medical Ltd., et al.,* 2:02–cv–08269–ABC–PLA, C.D. CA.—Declaration of Robert Anderson in Support of Plaintiffs' Ex Parte Application for Temporary Restraining order and Order to show Cause re Preliminary Injunction (Nov. 1, 2002).

*Lumenis Ltd., et al. v. Syneron Medical Ltd., et al.,* 2:02–cv–08269–ABC–PLA, C.D. CA.—Declaration of Sarit Moussayoff in Support of Plaintiffs' Motion for Preliminary Injunction (May 20, 2003).

*Lumenis Ltd., et al. v. Syneron Medical Ltd., et al.,* 2:02–cv–08269–ABC–PLA, C.D. CA.—Declaration of Shimon Eckhouse in Support of Opposition to Plaintiffs' Ex Parte Application for Temporary Restraining Order to Show Cause Re Preliminary Injunction (Nov. 1, 2002).

*Lumenis Ltd., et al. v. Syneron Medical Ltd., et al.,* 2:02–cv–08269–ABC–PLA, C.D. CA.—Plaintiff Lumenis Ltd. And Lumenis Inc.'s Ex Parte Application for Temporary Restraining Order to Show Cause Re Preliminary Injunction; Memorandum of Points and Authorities; Declarations of Alon Maor, Robert Anderson and Felix T. Woo; [Proposed] Order (Oct. 28, 2000).

*Lumenis Ltd., et al. v. Syneron Medical Ltd., et al.,* 2:02–cv–08269–ABC–PLA, C.D. CA.—Expert Report of Hon. Gerald J. Mossinghoff in support of Plaintiffs' Motion for Preliminary Injunction (May 20, 2003).

*Lumenis Ltd., et al. v. Syneron Medical Ltd., et al.,* 2:02–cv–08269–ABC–PLA, C.D. CA.—Syneron Medical Ltd.'s First Amended Answer to Plaintiffs' Complaint (Apr. 23, 2003).

*Lumenis Ltd., et al. v. Syneron Medical Ltd., et al.,* 2:02–cv–08269–ABC–PLA, C.D. CA.—Syneron Inc.'s First Amended Answer to Plaintiffs' Complaint (Apr. 23, 2003).

*Lumenis Ltd., et al. v. Syneron Medical Ltd., et al.,* 2:02–cv–08269–ABC–PLA, C.D. CA.—Plaintiffs' Memorandum of Points and Authorities in Support of Motion for Preliminary Injunction (Apr. 25, 2003).

*Lumenis Ltd., et al. v. Syneron Medical Ltd., et al.,* 2:02–cv–08269–ABC–PLA, C.D. CA.—Syneron's Memorandum of Points and Authorities in Opposition to Plaintiffs' Motion for a Preliminary Injunction (May 8, 2003).

*Lumenis Ltd., et al. v. Syneron Medical Ltd., et al.,* 2:02–cv–08269–ABC–PLA, C.D. CA.—Plaintiffs' Ex Parte Application for Temporary Restraining Order and Order to Show Cause Re Preliminary Injunction (Nov. 4, 2002).

*Lumenis Ltd., et al. v. Syneron Medical Ltd., et al.,* 2:02–cv–08269–ABC–PLA, C.D. CA.—Notice of Errata Re Plaintiffs' Ex Parte Application for Temporary Restraining Order to Show Cause Re Preliminary Injunction (Oct. 30, 2002).

*Lumenis Ltd., et al. v. Syneron Medical Ltd., et al.,* 2:02–cv–08269–ABC–PLA, C.D. CA.—Notice of Errata (Jan. 8, 2003).

*Lumenis Ltd., et al. v. Syneron Medical Ltd., et al.,* 2:02–cv–08269–ABC–PLA, C.D. CA.—Plaintiff's Notice of Lodging Opinion nad Tutorial of Court Appointed Expert Dr. Oscar M. Stafsudd (Apr. 25, 2003).

*Lumenis Ltd., et al. v. Syneron Medical Ltd., et al.,* 2:02–cv–08269–ABC–PLA, C.D. CA.—Notice of Response of Court Appointed Expert to Order Seeking Clarification (Jun. 16, 2003).

*Lumenis Ltd., et al. v. Syneron Medical Ltd., et al.,* 2:02–cv–08269–ABC–PLA, C.D. CA.—Syneron Inc.'s Objection to Declaration of Robert Anderson Submitted in Support of Plaintiffs' Ex Parte Application for Temporary Restraining order and Order to Show Cause Re Preliminary Injunction (Nov. 1, 2002).

*Lumenis Ltd., et al. v. Syneron Medical Ltd., et al.,* 2:02–cv–08269–ABC–PLA, C.D. CA.—Defendant Syneron, Inc.'s Opposition to Plaintiffs' Ex Parte Application for Temporary Restraining Order and Order to Show Cause Re Preliminary Injunction (Nov. 1, 2002).

*Lumenis Ltd., et al. v. Syneron Medical Ltd., et al.,* 2:02–cv–08269–ABC–PLA, C.D. CA.—Plaintiffs' Motion for Preliminary Injunction (Jul. 11, 2003).

*Lumenis Ltd., et al. v. Syneron Medical Ltd., et al.,* 2:02–cv–08269–ABC–PLA, C.D. CA.—Plaintiffs' Motion for Preliminary Injunction (Aug. 5, 2003).

*Lumenis Ltd., et al. v. Syneron Medical Ltd., et al.,* 2:02–cv–08269–ABC–PLA, C.D. CA.—Reply of Plaintiffs Lumenis Ltd. And Lumenis Inc. in Support of Motion for Preliminary Injunction (May 22, 2003).

*Lumenis Ltd., et al. v. Syneron Medical Ltd., et al.,* 2:02–cv–08269–ABC–PLA, C.D. CA.—Reply Opinion Joseph T. Walsh, Jr. in support of Plaintiffs' Motion for Preliminary Injunction (May 20, 2003).

*Lumenis Ltd., et al. v. Syneron Medical Ltd., et al.,* 2:02–cv–08269–ABC–PLA, C.D. CA.—Syneron's Response Brief for Court–Appointed Expert Re: Claim Construction (Nov. 17, 2003).

*Lumenis Ltd., et al. v. Syneron Medical Ltd., et al.,* 2:02–cv–08269–ABC–PLA, C.D. CA.—Plaintiffs' Response Brief to Court–Appointed Expert (Jan. 9, 2003).

*Lumenis Ltd., et al. v. Syneron Medical Ltd., et al.,* 2:02–cv–08269–ABC–PLA, C.D. CA.—Submission of Materials for Court Appointed Expert Pursuant to the Parties' Joint Stipulation (Dec. 19, 2002).

*Lumenis Ltd., et al.* v. *Syneron Medical Ltd., et al.,* 2:02–cv–08269–ABC–PLA, C.D. CA.—Supplemental Declaration Of Alon Moar in Support of Plaintiff Lemenis, Inc.'s Motion for Preliminary Injunction (May 23, 2003).

*Lumenis Ltd., et al.* v. *Syneron Medical Ltd., et al.,* 2:02–cv–08269–ABC–PLA, C.D. CA.—Supplemental Declaration of Felix T. Woo in Support of Plaintiffs' Ex Parte Application for Temporary Restraining Order and Order to Show Cause Re Preliminary Injunction (Nov. 4, 2002).

*Lumenis Ltd., et al.* v. *Syneron Medical Ltd., et al.,* 2:02–cv–08269–ABC–PLA, C.D. CA.—Plaintiffs' Disclosures Persuant to Fed.R.Civ.P.26 Jan. 14, 2003).

*Lumenis Ltd., et al.* v. *Syneron Medical Ltd., et al.,* 2:02–cv–08269–ABC–PLA, C.D. CA.—Plaintiffs' Response to Synerons' First Set of Interrogatories (Jan. 13, 2003).

*Lumenis Ltd., et al.* v. *Alma Ltd., et al.,* 07:CV3622, N.D.Ill—Videotaped Deposition of Richard R. Anderson, M.D. (Dec. 13, 2007).

AcuLight HR, *Operator Manual,* PB 3581110 Revision B (Jul. 2001).

AestiLight™ Millenium, *Operator Manual,* PB 3381110 Revision A (Aug. 2003).

AestiLight™ Photo Epilation System, *AestiLight Service Manual,* PB 3380120 Revision B (Mar. 2000).

AestiLight™ Photo Epilation System, *Operator Manual,* PB 3380110 Revision A (May 1999).

EpiLight™ Hair Removal System, *Operator Manual,* PB 400–9001 Revision 9 (Aug. 2000).

EpiLight™ Hair Removal System, *Operator Manual,* PB 400–9001 Revision 2 (Jul. 1996).

EpiLight™ Hair Removal System, Operator Manual, PB 400–9001 Revision 5 (Aug. 1997).

EpiLight™ Hair Removal System, Operator Manual, PB 400–9001 Revision 4 (Jul. 1997).

EpiLight™ Hair Removal System, Operator Manual, PB 400–9001 Revision 1 (Jun. 1996).

EpiLight™ Hair Removal System, Operator's Manual, PB 400–9001 Revision 7 (Jan. 1998).

EpiLight™ Hair Removal System, Operator's Manual, PB 400–9001 Revision 6 (Dec. 1997).

EpiLight™ Hair Removal, Operator Manual, PB 400–9001 Revision 3 (Feb. 1997).

IPL Quantum HR, Operator's Manual, PB 3580110 Revision B (Jun. 2001).

IPL Quantum SR, Operator's Manual, PB 3580110 Revision A (Sep. 2000).

IPL™ Quantum DL, Operator's Manual, PB 3580110 Revision B (Jul. 2002).

IPL™ Quantum HR, Operator's Manual, PB 3580110 Revision D (Jul. 2002).

IPL™ Quantum HR, Operator's Manual, PB 3580110 Revision C (Dec. 2001).

IPL™ Quantum SR, Operator Manual, PB 3680110 Revision D (Oct. 2002).

Lumenis IPL™ Quantum, *Service Manual,* (Mar. 2002).

PhotoDerm®, *Operator Manual,* PB 200–9001 Revision 1 (Jun. 1996).

PhotoDerm PL, *Operator Manual,* PB 200–9012 Revision A (May 1997).

PhotoDerm VL, *Operator Manual,* PB 100–9033 Revision A (May 1997).

PhotoDerm® VL, *Operator Manual,* (Jul. 1997).

PhotoDerm® VL, *Operator Manual,* PB 100–9001 Revision 2B (Oct. 1995).

PhotoDerm® VL, *Operator Manual,* PB 100–9001–1 Revision 1 (Apr. 1995).

PhotoDerm® VL/PL, *Operator's Manual,* PB 2180150 Revision B (May 1998).

PhotoDerm® VL/PL, *Service Manual,* PB 100–9022 Revision 2 (Nov. 1996).

PhotoDerm® VL/PL/HR, *Operator Manual,* PB 2280150 Revision B (May 1998).

TwoHead PhotoDerm®, *Service Manual,* (Apr. 2000).

VascuLight EPI Mode, *Operating Instructions,* PB 2300410 Revision C (Dec. 2001).

VascuLight™ Elite, *Operator's Manual,* PB 2780110 Revision A (Oct. 2002).

VascuLight™, *Operator Manual,* PB 2380150 Revision B (2001).

Epilight® Hair Removal System, *Service Manual,* PB4009007 Revision B (Jan. 1999).

AcuLight™ *Operator's Manual,* PB3581110 Revision 0 (Feb. 2001).

IPL Quantum HR, *Operator Manual,* PB3580110 Revision A (Jun. 2000).

Epilight® Hair Removal System, *Operator Manual,* PB4009001 Revision (Nov. 1998).

ESC Medical, "New Photo–Epilation Technique for Hair Removal", *Medco Forum,* 4(13) (Sep. 1997).

Reliant Technologies, Inc. Product News,Accu–Scan, Multi–Wavelength Laser Scanning System for CO2, Jan. 25, 1995, 3 pages.

Sharplan Swiftlase Flashscan, Jun. 1993.

UNILASE A new CO2 Laser for Microsurgery, I.L. Med. Newsletter, vol. 1, No. 3, Spring 1991.

I. L. Med. Unilase System Brochure (1993).

Achauer et al., "Argon Laser Treatment of Telangiectasia of the Face and Neck: 5 Years' Experience", *Lasers Surg. Med.,* 7:495–498 (1987).

Alora et al., "Recent Developments in Cutaneous Lasers", *Lasers Surg. Med.,* 26:108–118 (2000).

Alster et al., "Treatment of Port–Wine Stains with the Flashlamp–pumped Pulsed Dye Laser: Extended Clinical Experience in Children and Adults", *Ann. Plast. Surg.,* 32(5):478–484 (1994).

Altshuler et al., "Extended Theory of Selective Photothermolysis", *Lasers Surg. Med.,* 29:416–432 (2001).

Ambrose et al., "Prospective randomized comparison of photocoagulation and rubber band ligation in treatment of haermorrhoids", *Br. Med. J.,* 286:1389–1391 (1983).

Anderson et al., "Mechanisms of Selective Vascular Changes Caused by Dye Lasers",*Lasers Surg. Med.,* 3:211–215 (1983).

Anderson et al., "Microvasculature Can Be Selectively Damaged Using Dye Lasers: A Basic Theory and Experimental Evidence in Human Skin",*Lasers Surg. Med.,* 1:263–276 (1981).

Anderson et al., "Selective Photothermolysis: Precise Microsurgery by Selective Absorption of Pulsed Radiation", *Science,* 220:524–527 (1983).

Anderson, T.F., "Light Sources in Photomedicine", in *Clinical Photomedicine,* Chapter 3, pp. 37–58, Marcel Dekker, Inc., New York (1993).

Angermeier, M.C., "Treatment of facial vascular lessions with intense pulsed light", *J. Cutan. Laser Ther.,* 1:95–100 (1999).

Anvari et al., "Selective cooling of biological tissues: application for thermally mediated therapeutic procedures", *Phys. Med. Biol.*, 40:241–252 (1995).

Apfelberg et al., "Comparison of Argon and Carbon Dioxide Laser for Treatment of Decorative Tattoos Clinical and Pathological Observations", *Lasers Surg. Med.*, 3:183 (Abstract No. 294) (1983).

Apfelberg et al., Dot or Pointillistic Method for Improvement in Results of Hypertrophic Scarring in the Argon Laser Treatment of Portwine Hemangiomas,*Lasers Surg. Med.*, 6:552–558 (1987).

Apfelberg et al., "Investigation of YAG Laser Uses in Plastic Surgery", *Lasers Surg. Med.*, 6:246 (Abstract No. 77) (1986).

Apfelberg et al., "Preliminary Investigation of KTP/532 Laser Light in the Treatment of Hemangiomas and Tattoos", *Lasers Surg. Med.*, 6:38–42 (1986).

Apfelberg et al., "Progress Report on Extended Clinical Use of the Argon Laser for Cutaneous Lessions", *Lasers Surg. Med.*, 1:71–83 (1980).

Apfelberg et al., "Progress Report on Multicenter Study of Laser–Assisted Liposuction", *Aesth. Plast. Surg.*, 29:259–264 (1994).

Apfelberg et al., "Results of Argon and CO2 Laser Exposure of Telagiectasia of the Lower Extremity: A Preliminary Report", *Lasers Surg. Med.*, 3:149 (Abstract No. 165) (1983).

Apfelberg et al., "Study of Three Laser Systems for Treatment of Superficial Varicosities of the Lower Extremity", *Lasers Surg. Med.*, 7:219–223 (1987).

Apfelberg et al., "Superpulse $CO_2$ Laser Treatment of Facial Syringomata", *Lasers Surg. Med.*, 7:533–537 (1987).

Apfelberg et al., "Update on Laser Usage in Treatment of Decorative Tattoos", *Lasers Surg. Med.*, 2:169–177 (1982).

Apfelberg, D.B., "Intralesional Laser Photocoagulation— Steroids as an Adjunct to Surgery for Massive Hemangiomas and Vascular Malformations",*Ann. Plast. Surg.*, 35:144–148 (1995).

Ara et al., "Irradiation of Pigmented Melanoma Cells with High Intensity Pulsed Radiation Generates Acoustic Waves and Kills Cells", *Lasers Surg. Med.*, 10:52–59 (1990).

Ashinoff et al., "Cappillary Hemangiomas and Treatment with the Flash LampPumped Pulsed Dye Laser",*Arch. Dermatol.*, 127:202–205 (1991).

Ashinoff et al., "Flashlamp–pumped pulsed dye laser for port–wine stains in infancy: Earlier versus later treatment",*J. Am. Acad. Dermatol.*, 24:467–472 (1991).

Bell et al., "100 μsec pulsed $CO_2$ laser resurfacing of lower eyelids: Erythema and rhytides reduction", *SPIE*, 2970:360–366 (1997).

Broska et al., "Comparison of the Argon Tunable Dye Laser with the Flashlamp Pulsed Dye Laser in Treatment of Facial Telangiectasia", *J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–594 (1991).

Burson et al., "Gel de Transmission de Ultrasonidos: Estudio Comparativo de Distintas Formulaciones", *Farm Hosp.*, pp. 394–399 (1991) (in Spanish, with English Abstract Only).

Cates, M.C., "A long pulse (5μs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremities",*J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL",*J. Cutan. Laser Ther.*, 1:101–104 (1999).

Cole–Beuglet et al., "Ultrasound mammography for the Augmented Breast",*Radiology*, 146:737–742 (1983).

Colver et al., "Port Wine Stains", *Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "History of Photodynamic Therapy",*Aust. N. Z. J. Surg.*, 61:340–348 (1991).

Denham et al., "Light Distribution in Laser Irradiated Tissue", *Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulus et al., "High–energy Short–pulse Flashlamps: Operating Characteristics", *Applied Optics*, 16:70–75 (1977).

Ell et al., "Laser Lithotripsy of Gallstone by Means of a Pulsed Neodymium YAG Laser—In Vitro and Animal Experments", *Endoscopy*, 18:92–94 (1986).

Englehardt et al., "Spectroscopy During Laser Induced Shock Wave Lithotripsy",*SPIE*, 906:200–204 (1988).

Fitzpatrick et al., "Flashlamp–pumped Pulsed Dye Laser Treatment of Port–Wine Stains", *J. Dermatol. Surg. Oncol.*, 20:743–748 (1994).

Fitzpatrick et al., "Treatment of Leg Veins: A Comparison of Laser Therapy with a Noncoherent, Multiwave Light Source", *Proc. Ann. Meeting IEEE Lasers & Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study", *Lasers Med. Sci.*, 8:185–196 (1993).

Foster et al., "The Successful Use of the PhotoDerm VL in the Treatment of a Cavernous Hemangioma in a Dark–Skinned Infant", *Minimally Invasive Surgical Nursing*, 10:102–104 (1996).

Garden et al., "Effect of Dye Laser Pulse Duration on Selective Cutaneous Vascular Injury",*J. Invest. Dermatol.*, 87(5):653–657 (1986).

Garden et al., "The Treatment of Port–wine Stains by the Pulsed Dye Laser Analysis of Pulse Duration and Long–term Therapy", *Arch. Dermatol.*, 124:889–896 (1988).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Lasers Surg. Med.*, 11:287–296 (1991).

Gijsbers et al., "Effect of Force on Ablation Depth for a XeCl Excimer Laser Beam Delivered by an Optical Fiber in Contact with Arterial Tissue Under Saline", *Lasers Surg. Med.*, 12:576–584 (1992).

Gilbert, D.J., "Incorporating Photodynamic Therapy Into a Medicinal and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long–Term Hair Removal", *J. Cutan. Laser Ther.*, 1:167–171 (1999).

Gold et al., "Treatment of Wrinkles and Skin Tightening Using Aluma™ Skin Renewal System with FACES™ (Functional Aspiration Controlled Electrothermal Stimulation) Technology",*Aesthetic Buyers Guide*, pp. 1–6 (2005).

Gold, M.H., "Aminolevulinic Acid Photodynamic Therapy: Medical Evidence for Its Expanded Use", *Expert Rev. Med. Devices*, 3:357–371 (2006).

Gold, M.H., "Introduction to Photodynamic Therapy: Early Experience", *Dermatol. Clin.*, 25:1–4 (2007).

Goldberg et al., "Nonablative Treatment of Rhytids With Intense Pulsed Light", *Lasers Surg. Med.*, 26:196–200 (2000).

Goldberg et al., "Q–switched Nd:YAG Laser: Rhytid Improvement by Non–Ablative Dermal Remodelling", *J. Cutan. Laser Ther.*, 2:157–160 (2000).

Goldberg, D.J., "Effect of Temperature–Controlled Cooling on Light–Based Skin Treatments", *J. Cos. Laser Ther.*, 8:155–156 (2006).

Goldberg, D.J., "Erbium: YAG Laser Resurfacing: What Is Its Role?", *Aesth. Surg. J.*, 18(4):255–260 (1998).

Goldberg, D.J., "New Coolagen Formation After Dermal Remodelling with an Intense Pulsed Light Source", *J. Cutan. Laser Ther.*, 2:59–61 (2000).

Goldman et al., "600 mm Flash Pumped Dye Laser for Fragile Telengiectasia of the Elderly",*Lasers Surg. Med.*, 13:227–233 (1993).

Goldman et al., "Photothermal Sclerosis of Leg Veins", *Dermatol. Surg.*, 22:323–330 (1996).

Goldman et al., "Pulsed dye laser treatment of telangiectases with and without subtherapeutic sclerotherapy", *J. Am. Acad. Dermatol.*, 23(1):23–30 (1990).

Goldman et al., "Treatment of Cutaneous Vascular Lesions", in *Cutaneous Laser Surgery*, Chapter 2, pp. 19–105 (1994).

Goldman et al., "Treatment of port–wine stains (capillary malformation) with the flashlamppumped pulsed dye laser", *J. Pediatrics*, 122(1):71–77 (1993).

Goldman, M.P., "Laser and Noncoherent Pulsed Ligth Treatment of Leg Telangiectasia and Venules", *Cos. Dermatol.*, 8(10):43–44 (1995).

Goldman, M.P., "Sclerotherapy Treatment for Varicose and Telangiectatic Leg Veins", in *Vascular and Pigmented Abnormalities*, Chapter 17, pp. 256–271 (1997).

Gomer, H., "Military laser burns away skin flaws", *The London Sunday Times*, No. 8929 (Oct. 15, 1995).

Gonzalez et al., "Treatment of telangiectases and other benign vascular lesions with the 577 nm pulsed dye laser", *J. Am. Acad. Dermatol.*, 27(2):220–226 (1992).

Gregory et al., "Effect of Blood Upon the Selective Ablation of Atherosclerotic Plaque with a Pulsed Dye Laser", *Lasers Surg. Med.*, 10:533–543 (1990).

Grevelink et al., "Update on the Treatment of Benign Pigmented Lesions with the Q–Switched Ruby Laser", *Laser Surg. Med.*, 4:73–74 (Abstract No. 326) (1992).

Groot et al., "Comparison of the infrared coagulator and the carbon dioxide laser in the removal of decorative tattoos", *J. Am. Acad. Dermatol.*, 15:518–522 (1986).

Gustafsson et al., "A Variable Pulsewidth Vascular System for Dermatology", *SPIE*, 2128–188–196 (1994).

Guttman, C., "Novel radiofrequency–based treatment achieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE*, 2671:211–218 (1996).

Henderson, B.W., "Photodynamic therapy—coming of age", *Photodermatology*, 6:200–211 (1989).

Henning et al., "Clinical and Histological Evaluation of Portwine Stain Treatment with a Microsecond pulsed Dye–laser at 577 NM", *Lasers Surg. Med.*, 4:375–380 (1984).

Henning et al., "Port Wine Stain Coagulation Experiments with a 540–nm Continuous Wave Dye–laser", *Lasers Surg. Med.*, 2:205–210 (1983).

Henning et al., "Rhinophyma Treated by Argon Laser",*Lasers Surg. Med.*, 2:211–215 (1983).

Henning et al., "Treatment of Keloids and Hypertrofic Scars with an Argon Laser",*Lasers Surg. Med.*, 6:72–75 (1986).

Hilsenrath, J.E., "Investing it; Unsightly Veins? Zap. Wall St. Woes? Zap", *New York Times*, http://www.nytimes.com, pp. 1–3 (Jun. 23, 1996).

Hruza et al., "Laser Skin Resurfacing", *Arch. Dermatol.*, 132:451–455 (1996).

Hughes, P.S.H., "Multiple Miliary Osteomas of the Face Ablated With the Erbium: YAG Laser",*Arch. Dermatol.*, 135:378–380 (1999).

"Infrared–Coagulator", Lumatec product leaflet, pp. 1–4.

Ishimaru, A., "Diffusion of light in turbid material", *Applied Optics*, 28(12):2210–2215 (1989).

Jacques, S.L., "The Role of Skin Optics in Diagnostic and Therapeutic Uses of Lasers", *Lasers Dermatol.*, pp. 1–21 (1992).

Jaitly et al., "1 MV Long Pulse Generator with Low Ripple and Low Droop",$8^{th}$ *IEEE Int'l Pulsed Power Conf.*, pp. 161–165 (1991).

Jaitly et al., "Design and Testing of Multi–output 300kV Prototype Induction Cell Pulsed Power Supply for Darht", $10^{th}$ *IEEE Int'l Pulsed Power Conf.*, pp. 1412–1421 (1995).

Jay, H.H., "Victory Over Veins", http://www.nytimes.com, pp. 1–2 (Jul. 21, 1996).

Johannigmann et al., "Ein Neues Ultraschall–Kontakgel", *Geburtsh. U. Frauenheilk*, p. 34 (1974) (in German, with English Abstract Only).

Kalka et al., "Photodynamic Therapy in Dermatology",*J. Am. Acad. Dermatol.*, 42:389–413 (2000).

Kaminester, L.H., "Suntanning Centers", *JAMA*, 244(11):1258–1259 (1980).

Kaufmann et al., "Pulsed 2–94–μm erbium–YAG laser skin ablation–experimental results and first clinical application", *Clin. Exp. Dermatol.*, 15:389–393 (1990).

Keijzer et al., "Laser Beam Diameter for Port Wine Stain Treatment", *Lasers Surg. Med.*, 11:601–605 (1991).

Kennedy et al., "Photodynamic Therapy with Endogenous Protoporphyrin, IX: Basic Principles and Present Clinical Experience", *J. of Photochem. Photobio.*, 6:143–148 (1990).

Kilmer et al., "Pulse Dye Laser Treatment of Rhytids", *Lasers Surg. Med.*, p. 44 (Abstract No. 194) (1997).

Koechner, W., in *Solid State Laser Engineering*, Springer Series in Optical Sciences—vol. 1, Chapters 1–2, pp. 1–620, Springer–Verlag, New York (1976).

Lakmaker et al., "Modeling the Color Perception of Port Wine Stains and its Relation to the Depth of Laser Coagulated Blood vessels", *Lasers Surg. Med.*, 13:219–226 (1993).

Lash et al., "How We Got Here", *Lasers Surg. Med.*, 3:113 (Abstract No. 29) (1983).

Lask et al., "Laser Skin Resurfacing with the SikTouch Flachscanner for Facial Rhytides", *Dermatol. Surg.*, 21:1021–1024 (1995).

Lask et al., "Nonablative laser treatment of faical rhytides", *SPIE*, 2970–338–349 (1997).

Levins et al., "Q–Switched Ruby Laser Treatment of Tattoos", *Lasers Surg Med.*, Suppl. 3:63–64 (Abstract No. 255) (1991).

Lowe et al., "Skin Resurfacing with the Ultrapulse Carbon Dioxide Laser",*Dermatol. Surg.*, 21:1025–1029 (1995).

Magee et al., "Vein Marking Through Ultrasound Coupling Gel",*Eur. J. Vasc. Surg.*, 4:491–492 (1990).

Majaron et al., "Deep Coagulation of Dermal Collagen with Repetitive Er:YAG Laser Irradiation", *Lasers Surg. Med.*, 26:215–222 (2000).

Majaron et al., "Er:YAG Laser Skin Resurfacing Using Repetitive Long–Pulse Exposure and Cryogen Spray Cooling: I. Histological Study", *Lasers Surg. Med.*, 28:121–130 (2001).

Majaron et al., "Er:YAG Laser Skin Resurfacing Using Repetitive Long–Pulse Exposure and Cryogen Spray Cooling: II. Theoretical Analysis", *Lasers Surg. Med.*, 28:131–137 (2001).

Margolis et al., "Visible Action Spectrum for Melanin–Specific Selective Photothermolysis", *Lasers Surg. Med.*, 9:389–397 (1989).

Marchic et al., "White–Light Flashlamp–pumped dye laser for photography through endoscopes", *Optics Communications*, 45(1):21–25 (1983).

McCaughan et al., "Photodynamic Therapy for Cutaneous and Subcutaneous Malignant Neoplasms", *Arch. Surg.*, 124:211–216 (1989).

McCaughan et al., "Photodynamic Therapy: An Eight Year Experience", in *Photodynamic Therapy: Basic Principles and Clinical Applications*, pp. 323–331 (1992).

Meijering et al., "Limits of Radial Time Constants to Approximate Thermal Response of Tissue", *Lasers Surg. Med.*, 13:685–687 (1993).

Miller et al., "Optical Modelling of Light Distributions in Skin Tissue Following Laser Irradiation", *Lasers Surg. Med.*, 13:565–571 (1993).

Milner et al., "Analysis of nonablative skin resurfacing", *SPIE*, 2970:367–373 (1997).

Mordon et al., "Rationale for Automatic Scanners in Laser Treatment of Port wine Stains", *Lasers Surg. Med.*, 13:113–123 (1993).

Morelli et al., "Tunable Dye Laser (577 nm) Treatment of Port Wine Stains", *Lasers Surg. Med.*, 6:94–99 (1986).

Motamedi et al., "Thermal Response of Tissue During Laser Angioplasty", *Lasers Surg. Med.*, 5:172 (Abstract No. 114) (1985).

Mutzhas et al., "A New Apparatus with High Radiation Energy Between 320–460 nm: Physical Description and Dermatological Applications",*J. Invest. Dermatol.*, 76:42–47 (1981).

Nakagawa et al., "Ultrastructural Changes in Human Skin After Exposure to a Pulsed Laser",*J. Invest. Dermatol.*, 84(5):396–400 (1985).

Nestor et al., "New Perspective on Photorejuvenation", *Skin & Aging*, 11:68–74 (2003).

Newman et al., "Variable Pulse Erbium: YAG Laser Skin Resurfacing of Perioral Rhytides and Side–by–side Comparison with Carbon Dioxide Laser", *Lasers Surg. Med.*, 26:208–214 (2000).

Parrish et al., "Exploring Mechanisms of Specificity in Laser–Tissue Interactions", *Lasers Surg. Med.*, 3:175 (Abstract No. 260) (1983).

Parrish et al., "Spatial Confinement of Thermal Effects of Pulsed Laser Irradiation of Tissue", *Lasers Surg. Med.*, 3:157 (Abstract No. 195) (1973).

Paul et al., "The Effect of Temperature and Other Factors on Selective Microvascular Damage Caused by Pulsed Dye Laser", *J. Invest. Dermatol.*, 81(4):333–336 (1983).

Pfefer et al., "Mechanisms of Laser–Induced Thermal Coagulation of Whole Blood in vitro", *SPIE*, 3590:20–31 (1999).

Philipp et al., "Treatment of Congenital Vascular Disorders: Classification, Step Programme and Therapeutical Procedures", *SPIE*, 2086–228–238 (1993).

Pickering et al., "585 nm for the Laser Treatment of Port Wine Stains: A Possible Mechanism",*Lasers Surg. Med.*, 11:616–618 (1991).

Plewig et al., "A new apparatus for the delivery of high intensity UVA and UVA + UVB irradiation, and some dermatological applications", *Br. J. Dermatol.*, 98:15–24 (1978).

Polla et al., "Tunable Pulsed Dye Laser for the Treatment of Benign Cunaeous Vascular Ectasia", *Dermatologica*, 174:11–17 (1987).

Pottier et al., "Assessment of Non–Coherent Light Sources for Photodynamic Therapy", *SPIE*, 2371:364–368 (1995).

Pratesi, R., "Potential Use of Incoherent and Coherent Light–Emitting Diode (LEDs) in Photomedicine", in *Photomedicine, Laser Photobiol. Photmed.*, 22:293–308 (1983).

Ramrus et al., "A Compact One–Half MV Rep–Rate Pulser", $20^{th}$ *IEEE Power Modulator Symposium*, pp. 68–71 (1992).

Ramrus et al., "Design and Performance of a One–Half MV Rep–Rate Pulser", Proc. Of the $8^{th}$ IEEE International Pulsed Power Conference, pp. 982–985 (1991).

Ranganathan et al., "Promises for Ultrasonic Waves on Activity of Silica Gel and Some Supported Catalystes", *Ind. Eng. Chem. Prod. Res. Develop.*, 12:155–158 (1973).

Rassing et al., "Measurement of Ultrasonic Absorption in a Gel by Light Diffraction and Resonator Methods", *J. Mol. Liq.*, 26:97–108 (1983).

Rastegar et al., "Technique for Measurement of One–Dimensional Instantaneous Ablation Velocity", *Lasers Surg. Med.*, 8:533–535 (1988).

Raulin et al., "Treatment of a Nonresponding Port–Wine Stain With a New Pulsed Light Source (PhotoDerm® VL)", *Laser Surg. Med.*, 21:203–208 (1997).

Raulin et al., "Treatment of Adult Port–Wine Stains Using Intense Pulsed Light Therapy (PhotoDerm VL), Brief Initial Clinical Report", *Dermatol Surg.*, 23:594–601 (1997).

Raulin et al., "Treatment of benign venous malformation with an intense pulsed light source (PhotoDerm VL)", *Eur. J. Dermatol.*, 7:279–282 (1997).

Raulin et al., "Treatment of Essential Telangiectasias with an Intense Pulsed Light Source (PhotoDerm VL)", *Dermatol. Surg.*, 23:941–946 (1997).

Raulin et al., "Treatment of Port–wine Stains With a Noncoherent Pulsed Light Source", *Arch. Dermatol.*, 135:679–683 (1999).

Reyes et al., "Treatment of port–wine stains during childhood with the flashlamp–pumped pulsed dye laser", *J. Am. Acad. Dermatol.*, 23:1142–1148 (1990).

Ross et al., "Effects of $CO_2$ Laser Pulse Duration in Ablation and Residual Thermal Damage: Implications for Skin Resurfacing", *Lasers Surg. Med.*, 19:123–129 (1996).

Rowe, P.M., "Photodynamic therapy begins to shine", *Lancet*, 351:1496 (1998).

Sadick et al., "Photorejuvenation with Intense Pulsed Light: Results of a Multi–Center Study", *J. Drugs Dermatol.*, 3(1):41–49 (2004).

Sadick, N.S., "A Structural Approach to Nonablative Rejuvenation", *Cosmetic Dermatol.*, 15(12):39–43 (2002).

Sadick, N.S., "Update on Non–Ablative Light Therapy for Rejuvenation: A Review", *Lasers Surg. Med.*, 32:120–128 (2003).

Schamiloglu et al., "Modern Pulsed Power: Charlie Martin and Beyond", *Proceedings of the IEEE*, 92(7):1014–1020 (2004).

Schroeter et al., "An Intense Light Source: The Photoderm VL–Flashlamp as a New Treatment Possibility for Vascular Skin Lesions", *Dermatol. Surg.*, 24:743–748 (1998).

Schroeter et al., "Clinical significance of an intense, pulsed light source on leg telangiectasias of up to 1mm diameter", *Eur. J. Dermatol.*, 7:38–42 (1997).

Schroeter et al., "Photoderm VL treatment of leg teleangiectasia", *JEADV*, 5(Suppl. 1):S49 (Abstract No. W76) (1995).

Schwimer et al., "The Effect of Ultrasound Coupling Gels on Sperm Motility In Vitro", *Fertil. Steril.*, 42:946–947 (1984).

Sheehan et al., "Arrest of Embryo Development by Ultrasound Coupling Gels", *Feril. Sterol.*, 45:568–571 (1986).

Smith et al., "532–Nanometer Green Laser Beam Treatment of Superficial Varicosities of the Lower Extremeties", *Lasers Surg. Med.*, 8:130–134 (1988).

Steiger et al., "Comparison of Different Pulsed and Q–switched Solid–state Laser Systems for Endoscopic Laser Induced Shock Wave Lithotripsy: Performance and Laser/Stone Interactions", *SPIE*, 2300:94–101 (1990).

Strickland et al., "A 5kV, 250 kA Rep–Rated Pulser Using Parallel Ignitions", *7th IEEE Int'l Pulsed Conf.*, pp. 729–731 (1989).

Sunde et al., "Traumatic Tattoo Removal: Comparison of Four Treatment Methods in an Animal Model with Correlation to Clinical Experience", *Lasers Surg. Med.*, 10:158–164 (1990).

Svaasand et al., "Light and Drug Distribution with Topically Administered Photosensitizers", *Lasers Surg. Med.*, 11:261–265 (1996).

Szeimies et al., "A Possible New Incoherent Lamp for Photodynamic Treatment of Superficial Skin Lesions", *Acta Derm. Venereol (Stockh).*, 74:117–119 (1994).

Tan et al., "Action Spectrum of Vascular Specific Injury Using Pulsed Irradiation", *J. Invest. Dermatol.*, 92(60):868–871 (1989).

Tan et al., "EMLA for Laser Treatment of Portwine Stains in Children", *Lasers Surg. Med.*, 12:543–548 (1992).

Tan et al., "Histologic Responses of Port–wine Stains Treated by Argon, Carbon Dioxide, and Tunable Dye Lasers", *Arch. Dermatol.*, 122:1016–1022 (1986).

Tan et al., "Pulsed Dye Laser Treatment of Recalcitrant Verrucae: A Preliminary Report", *Lasers Surg. Med.*, 13:127–137 (1993).

Tan et al., "Treatment of Children with Port–Wine Stains Using the Flashlamp–Pulsed Tunable Dye Laser", *N. Engl. J. Med.*, 320(7):416–421 (1989).

Taub, A.F., "Photodynamic Therapy: Other Uses", *Dermatol. Clin.*, 25:101–109 (2007).

Taylor et al., "Q–Switched Ruby Laser (QSRL) Irradiation of Benign Pigmented Lesions: Dermal vs. Epidermal", *Lasers Surg. Med.*, 3:65 (Abstract No. 262) (1991).

Templeton et al., "Comparison of infrared coagulation and rubber band ligation for first and second degree haemorrhoids: a randomized prospective clinical trial", *Br. Med. J.*, 286:1387–1389 (1983).

Troccoli et al., "Multiple–Pulse Photocoagulation of Blood Vessels With A 585 Nm Tunable Laser", *Lasers Surg. Med.*, 4:3 (Abstract No. 2) (1992).

van Gemert et al., "Can Physical Modelling Lead to an Optimal Laser Treatment Strategy for Port–Wine Stains", in *Laser Applications in Medicine and Biology*, Chapter 5, pp. 199–247, Plenum Press, New York (1991).

van Gemert et al., "Instantaneous Ablation Behavior of In–Vitro Rods During Laser Irradiation", *Lasers Surg. Med.*, 5:136 (Abstract No. 4) (1985).

van Gemert et al., "Is There an Optimal Laser Treatment for Port Wine Stains", *Lasers Surg. Med.*, 6:76–83 (1986).

van Gemert et al., "Wavelengths for Laser Treatment of Port Wine Stains and Telagieactasia", *Lasers Surg. Med.*, 16:147–155 (1995).

"Varicose Vein Device Producer come to U.S. Market", *Clinica*, 687:9 (Jan. 8, 1996).

Venning et al., "Tattoo removal using infra–red coagulation: a dose comparison", *Br. J. Dermatol.*, 117:99–105 (1987).

Wagner et al., "Percutalgine–Gel et Ultrasonotherapie en Pathologie du Sport", *La Revue de Medecine*, 32:1681–1683 (1982) (in French, with English Abstract Only).

Waldorf et al., "Skin Resurfacing of Fine to Deep Rhytides Using a Char–free Carbon Dioxide Laser in 47 Patients", *Dermatol. Surg.*, 21:940–946 (1995).

Walsh et al., "Er:YAG Laser Ablation of Tissue: Measurement of Ablation Rates", *Lasers Surg. Med.*, 9:327–337 (1989).

Walsh et al., "Pulsed $CO_2$ Laser Tissue Ablation: Effect of Tissue Type and Pulse Duration On Thermal Damage", *Lasers Surg. Med.*, 8:108–118 (1988).

Walsh, J.T., "Er:YAG Laser Ablation of Tissue: Effect of Pulse Duration and Tissue Type on Thermal Damage", *Lasers Surg. Med.*, 9:314–326 (1989).

Walsh, J.T., "Pulsed Laser Ablation of Tissue: Analysis of the Removal Process and Tissue Healing", *Unpublished Ph.D. dissertation Massachussetts Institute of Technology, on file with Institute Archives and Hayden Library, Massachusetts Institute of Technology*, pp. 1–312 (1988).

Weiss et al., "Rejuvenation of Photoaged Skin: 5 Years Results with Intense Pulsed Light of the Face, Neck, and Chest", *Dermatol. Surg.*, 28:1115–1119 (2002).

Welch et al., "Practical Models for Light Distribution in Laser–Irradiated Tissue", *Lasers Surg. Med.*, 6:488–493 (1987).

Werner et al., "Die Hamangiombehandlung mit dem Neodym: Yttrium Aluminium–Granat Laser (Nd:YAG–Laser)", *Laryngo–Rhino–Otol.*, 71:388–395 (1992), (in German, with English Abstract Only).

West, T., "How Laser Surgery Can Help Your Rosacea Patients", *Skin & Aging,* pp. 43–46 (1998).

Wilder, D., "Pulsed 1064–nm Nd:YAG Laser Therapy for Noninvasive Treatment of a Massive Hemangioma: Case Report", *J. Clin. Laser Med. Surg.*, 17(6):245–247 (1999).

Wilson et al., "The physics of photodynamic therapy", *Phys. Med. Biol.*, 31(4):327–360 (1986).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 19–46 is confirmed.

Claims 1, 2 and 5–18 were previously cancelled.

\* \* \* \* \*